(12) United States Patent
Kulkarni et al.

(10) Patent No.: US 10,583,410 B2
(45) Date of Patent: Mar. 10, 2020

(54) AEROSOL PARTICLE GROWTH SYSTEMS USING POLYMER ELECTROLYTE MEMBRANES

(71) Applicants: The United States of America, as represented by the Secretary, Department of Health and Human Services, Bethesda, MD (US); Regents of the University of Minnesota, Minneapolis, MN (US)

(72) Inventors: Pramod S. Kulkarni, Mason, OH (US); Jikku Moolamkunnam Thomas, Minneapolis, MN (US); Christopher J. Hogan, Jr., Minneapolis, MN (US)

(73) Assignees: The United States of America, as Represented by the Secretary, Department of Health and Human Services, Bethesda, MD (US); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/325,986

(22) PCT Filed: Jul. 20, 2015

(86) PCT No.: PCT/US2015/041142
§ 371 (c)(1),
(2) Date: Jan. 12, 2017

(87) PCT Pub. No.: WO2016/011447
PCT Pub. Date: Jan. 21, 2016

(65) Prior Publication Data
US 2017/0157583 A1    Jun. 8, 2017

Related U.S. Application Data

(60) Provisional application No. 62/026,559, filed on Jul. 18, 2014.

(51) Int. Cl.
| | | |
|---|---|---|
| B01J 2/16 | (2006.01) | |
| G01N 15/06 | (2006.01) | |
| B01J 2/00 | (2006.01) | |

(52) U.S. Cl.
CPC ................. *B01J 2/16* (2013.01); *B01J 2/006* (2013.01); *G01N 15/065* (2013.01); *G01N 2015/0681* (2013.01)

(58) Field of Classification Search
CPC ........... B01J 2/006; B01J 2/16; G01N 15/065; G01N 2015/0681
(Continued)

(56) References Cited

U.S. PATENT DOCUMENTS 5,903,338 A * 5/1999 Mavliev ............... G01N 15/065
356/338
5,996,976 A 12/1999 Murphy et al.
(Continued)

FOREIGN PATENT DOCUMENTS

| JP | 01-035348 | 2/1989 |
|---|---|---|
| JP | 2006-170481 | 6/2006 |
| JP | 2013-190246 | 9/2013 |

OTHER PUBLICATIONS

Demokritou, et al., "A High Volume Apparatus for the Condensational Growth of Ultrafine Particles for Inhalation Toxicological Studies," *Aerosol Science & Technology*, 36:1061-1072 (Mar. 19, 2002).
(Continued)

*Primary Examiner* — Alexander M Weddle
(74) *Attorney, Agent, or Firm* — Klarquist Sparkman, LLP

(57) ABSTRACT

Disclosed herein are aerosol particle growth systems including polymer electrolyte membranes and related methods of increasing the size of aerosol particles. In some embodi-
(Continued)

ments, an outer housing contains a reservoir of a working fluid, and a PEM conduit extends through the outer housing, the reservoir, and the working fluid so that the working fluid is in contact with an outer surface of the PEM conduit. The conduit can be generally helical or coiled, for example. In some embodiments, the working fluid is molecularly transported across the PEM and disperses into an aerosol flowing through the PEM conduit. As the aerosol flows through the PEM conduit, the aerosol particles act as nucleation sites for the gaseous working fluid, which condenses on the particles, causing the particles to grow in size and making them easier to detect, collect, measure, count, study, or otherwise investigate.

30 Claims, 14 Drawing Sheets

(58) Field of Classification Search
USPC .......................................................... 427/212
See application file for complete search history.

(56) References Cited

U.S. PATENT DOCUMENTS

| | | | |
|---|---|---|---|
| 6,498,641 B1 | 12/2002 | Schildmeyer | |
| 6,712,881 B2 | 3/2004 | Hering et al. | |
| 7,622,216 B2 | 11/2009 | Halalay et al. | |
| 8,449,657 B2 | 5/2013 | Son et al. | |
| 2008/0083274 A1 | 4/2008 | Hering et al. | |
| 2008/0217158 A1 | 9/2008 | Rumpf et al. | |
| 2008/0311672 A1* | 12/2008 | Dasgupta | G01N 1/4005 436/161 |
| 2010/0319535 A1* | 12/2010 | Joshi | B01D 53/22 95/52 |
| 2013/0068632 A1* | 3/2013 | Chang | G01N 27/4146 205/780.5 |
| 2014/0033915 A1* | 2/2014 | Hering | B01D 47/00 95/1 |

OTHER PUBLICATIONS

Hering, et al., "A Laminar-Flow, Water-Based Condensation Particle Counter (WCPC)," *Aerosol Science & Technology*, 39:659-672 (2005).

Hoppel, et al., "A Segmented Thermal Diffusion Chamber for Continuous Measurements of CN," *Journal of Aerosol Science*, 10(4):369-373 (1979).

International Search Report and Written Opinion for related International Application No. PCT/US2015/041142, dated Sep. 30, 2015, 12 pages.

Kousaka, et al., "Development of a Mixing Type Condensation Nucleus Counter," *Journal of Aerosol Science*, 13(3):231-240 (1982).

Perma Pure et al., "MH-Series Humidifier User Manual," http://www.permapure.com/wp-content/uploads/2013/01/MH-Manual.pdf, 2 pages (Dec. 20, 2007).

Rozière et al., "Non-Flourinated Polymer Materials for Proton Exchange Membrane Fuel Cells," *Annu. Rev. Mater. Res.*, 33:503-555 (2003).

Shen, et al., "Microfluidic Protein Preconcentrator Using a Microchannel-Integrated Nafion Strip: Experiment and Modeling," *Analytical Chemistry*, 82(24):9989-9997 (Dec. 15, 2010).

Smitha et al., "Solid polymer electrolyte membranes for fuel cell applications—a review," *Journal of Membrane Science*, 259:10-26 (Jan. 21, 2005).

Stolzenburg, et al., "An Ultrafine Aerosol Condensation Nucleus Counter," *Aerosol Science and Technology* 14:48-65 (1991).

Wang, et al., "Fast Mixing Condensation Nucleus Counter: Application to Rapid Scanning Differential Mobility Analyzer Measurements," *Aerosol Science & Technology*, 36:678-689 (2002).

Zhao, et al., "Diffusion and Interfacial Transport of Water in Nafion," *The Journal of Physical Chemistry B*, 115:2717-2727 (Mar. 3, 2011).

Examination Report for related EP Application No. 15745058.6, dated May 17, 2019, 9 pages.

Japanese Office Action for related JP Application No. 2017-502679, dated May 16, 2019, 8 pages.

* cited by examiner

```
800
```

- 802 — PROVIDE PARTICLE GROWTH SYSTEM HAVING FIRST AND SECOND CHAMBERS
- 804 — INTODUCE WORKING FLUID INTO FIRST CHAMBER
- 806 — INTRODUCE AEROSOL INTO SECOND CHAMBER SEPARATED FROM FIRST CHAMBER BY A PEM
- 808 — HEAR A FIRST PORTION OF THE SECOND CHAMBER
- 810 — COOL A SECOND PORTION OF THE SECOND CHAMBER
- 812 — ALLOW WORKING FLUID TO BE MOLECULARLY TRANSPORTED ACROSS THE PEM INTO THE SECOND CHAMBER
- 814 — ALLOW WORKING FLUID TO CONDENSE ONTO AEROSOL PARTICLES IN THE SECOND CHAMBER
- 816 — DETECT, COLLECT, OR STUDY THE AEROSOL PARTICLES

FIG. 8

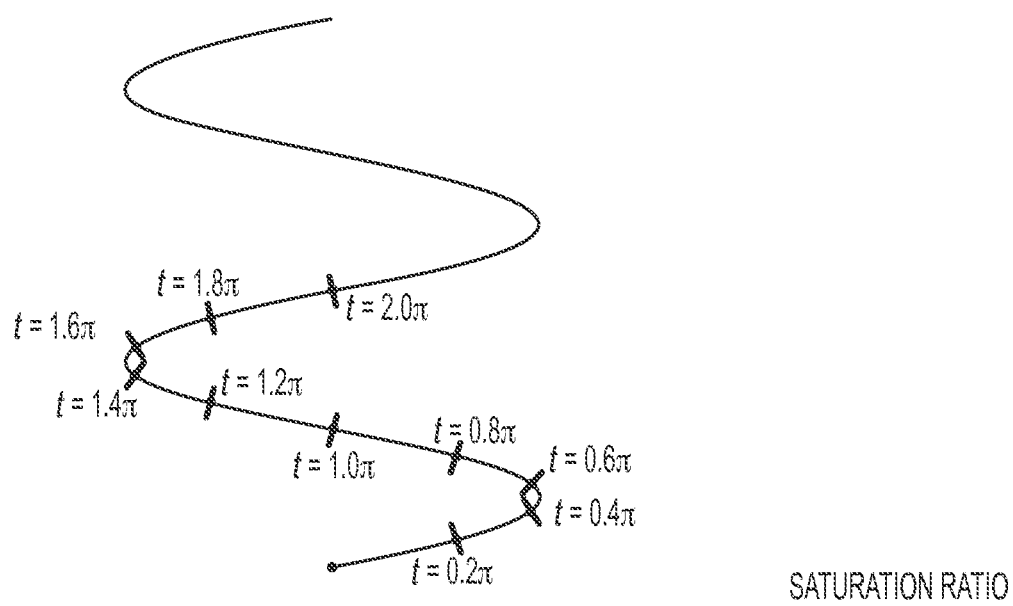
FIG. 11A
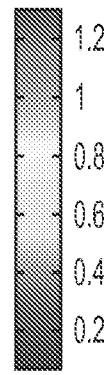
SATURATION RATIO
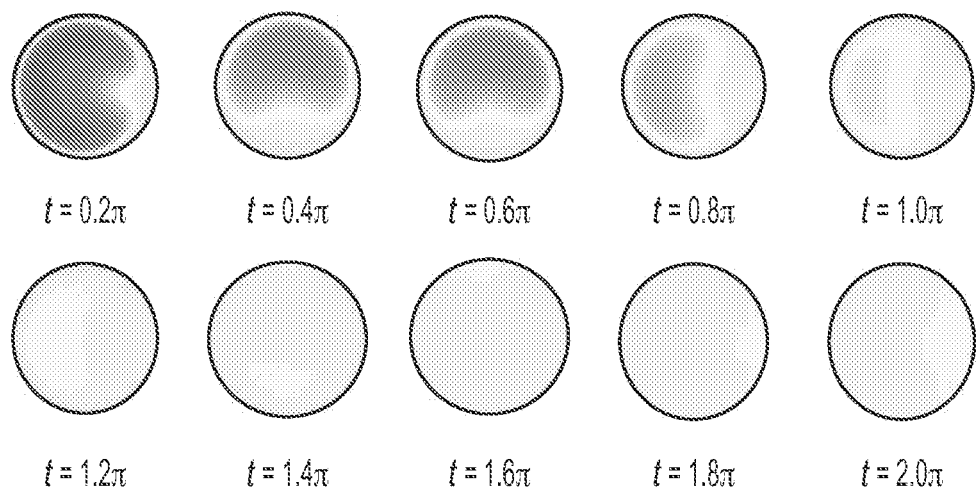
FIG. 11B

AEROSOL PARTICLE GROWTH SYSTEMS USING POLYMER ELECTROLYTE MEMBRANES

CROSS-REFERENCE TO RELATED APPLICATIONS

This is the U.S. National Stage of International Application No. PCT/US2015/041142, filed Jul. 20, 2015, which was published in English under PCT Article 21(2), and which claims the benefit of U.S. Provisional Patent Application No. 62/026,559 filed Jul. 18, 2014, which is incorporated by reference herein in its entirety.

ACKNOWLEDGMENT OF GOVERNMENT SUPPORT

This invention was made with government support under 214-2014-M-60655 awarded by the Centers for Disease Control. The government has certain rights in the invention.

FIELD

The present disclosure is directed to devices and methods for increasing the size of aerosol particles to facilitate their detection, collection, and analysis.

BACKGROUND

Exposure to hazardous airborne particles, particularly in ambient, industrial, and/or occupational atmospheres, poses a great health risk, and hazardous airborne particles can often be difficult to reliably detect, collect, and/or study. Particles smaller than about 300-400 nm in diameter are especially difficult to detect using known optical particle detection techniques. Some existing systems attempt to increase the size of aerosol particles to facilitate their identification and analysis, but these known systems are constrained in several respects. For example, known particle growth systems are often bulky and unsuitable for mobile or personal exposure sampling applications, in particular, because they are undesirably large, they require too much power, they cannot operate efficiently while in motion, and/or they cannot operate in a variety of spatial orientations. Thus, existing particle detection and measurement systems have certain drawbacks.

SUMMARY

In some embodiments, a particle growth system comprises an outer housing defining a liquid reservoir for containing a working liquid and a polymer electrolyte membrane conduit positioned at least partially within the outer housing and surrounded by the reservoir, wherein the conduit includes an inlet configured to receive a particle containing gas and an outlet configured to export the particle containing gas, wherein the system is operable to molecularly transport the working liquid into the conduit to promote particle growth in the conduit. In some embodiments, the conduit is substantially impermeable to the working liquid. In some embodiments, the particle growth system further comprises a heating element configured to heat the liquid in the reservoir. In some embodiments, the system further comprises a cooling device configured to cool a portion of the conduit.

In some embodiments, the working liquid is either liquid water or a liquid alcohol. In some embodiments, the system further comprises a particle detection system coupled to the outlet of the conduit. In some embodiments, the system further comprises a particle counting system coupled to the outlet of the conduit. In some embodiments, the system further comprises a particle analysis system coupled to the outlet of the conduit. In some embodiments, the system further comprises a particle collection system coupled to the outlet of the conduit. In some embodiments, the system further comprises a source of the particle-containing gas coupled to the inlet of the conduit. In some embodiments, the conduit comprises a porous support conduit not made from a polymer electrolyte membrane and a polymer electrolyte membrane substantially covering the pores of the porous support conduit to render the porous support conduit substantially impermeable to the working liquid in the reservoir.

In some embodiments, the conduit has a helical or coiled configuration. In some embodiments, the system further comprises a second polymer electrolyte membrane conduit positioned at least partially within the outer housing and surrounded by the reservoir. In some embodiments, the system is operable to molecularly transport the working liquid into the conduit by a mechanism consisting essentially of molecular transport of individual molecules of the working liquid across the membrane.

Some exemplary particle growth systems comprise a first microfabricated channel, having a first inlet and a first outlet, for containing a working liquid, a second microfabricated channel having a second inlet configured to receive a particle containing gas and a second outlet configured to export the particle containing gas, and a polymer electrolyte membrane portion separating the first channel from the second channel, wherein the system is operable to molecularly transport the working liquid into the second channel to promote particle growth in the second channel.

Some exemplary methods of growing particles in a particle growth system comprises providing a particle growth system having first and second chambers separated by a polymer electrolyte membrane, introducing a working fluid into the first chamber, introducing a particle containing gas into the second chamber, allowing the working fluid to be molecularly transported across the polymer electrolyte membrane into the second chamber, and allowing the working fluid to condense onto particles in the gas in the second chamber.

In some embodiments, the method further comprises maintaining a first portion of the second chamber at a first temperature and maintaining a second portion of the second chamber at a second temperature, wherein the first temperature is different from the second temperature. In some embodiments, the method further comprises collecting grown particles at an outlet of the second chamber. In some cases, the method further comprises detecting grown particles by optical means at an outlet of the second chamber. In some embodiments, the method further comprises counting grown particles at an outlet of the second chamber. In some embodiments, the method further comprises analyzing grown particles at an outlet of the second chamber.

The foregoing and other features and advantages of the disclosed technology will become more apparent from the following detailed description of several embodiments, which proceeds with reference to the accompanying figures.

BRIEF DESCRIPTION OF THE FIGURES

FIG. 8 illustrates a method of using a particle growth system including a PEM.

FIGS. 10A and 11A show a two-dimensional illustration of a helical growth tube, indicating the cut plane locations of the cross-sectional views of FIGS. 10B and 11B.

FIG. 11B shows contour plots of saturation ratios at various circular cross-sections along a helical growth tube with a second boundary condition.

DETAILED DESCRIPTION

Figure 1:
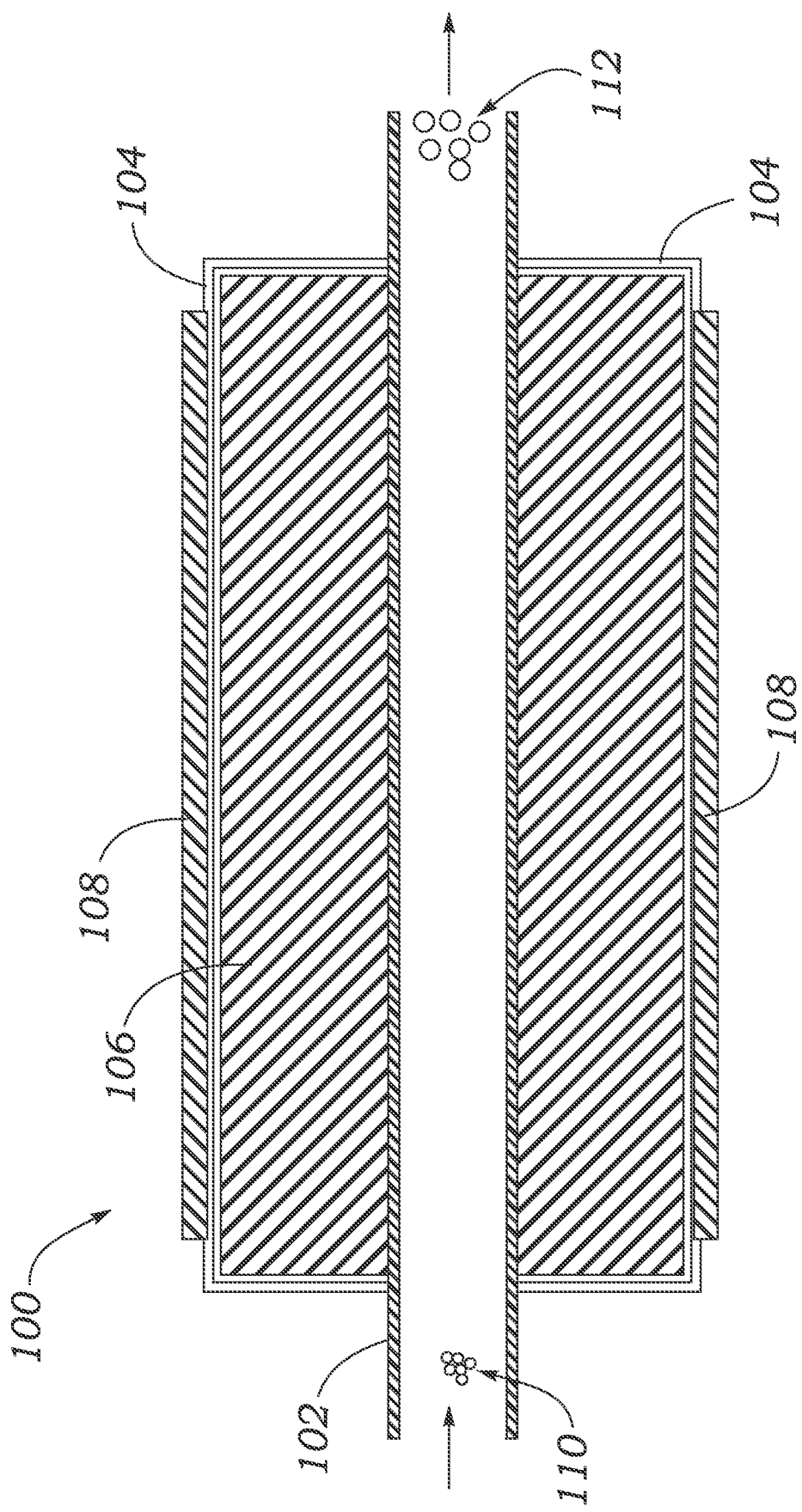
FIG. 1 is a schematic illustration of a first particle growth system including a straight PEM tube.

Disclosed herein are aerosol particle growth systems including polymer electrolyte membranes, also referred to as proton exchange membranes, or PEMs, and related methods of increasing the size of aerosol particles. In some embodiments, an outer housing contains a reservoir of a working fluid, and a PEM conduit or tube extends through the outer housing, the reservoir, and the working fluid so that the working fluid is in contact with an outer surface of the PEM conduit or tube. A conduit can comprise a channel through which an aerosol can flow, and can have any suitable cross-sectional shape, such as a circular, rectangular, square, triangular, cruciform, or other cross-sectional shape. In some embodiments, the working fluid is molecularly transported across the PEM and disperses into an aerosol flowing through the PEM conduit or tube. As the aerosol flows through the PEM conduit or tube, the aerosol particles act as nucleation sites for the vapors of the working fluid, which condenses on the particles, causing their condensational growth and making them easier to detect, collect, measure, count, study, or otherwise investigate. In some embodiments, the larger particles grown within the particle growth system are concentrated into small volumes of liquid to facilitate subsequent chemical or physical analyses of the particles.

These design advances allow particle growth systems to be smaller, higher throughput, less expensive, and/or more energy efficient than other known particle growth devices. Systems described herein can be functional in various spatial orientations, when subjected to motions, accelerations, and/or vibrations, and when subjected to relatively high working fluid pressures, unlike many prior devices in which random orientations, movements, and/or high working fluid pressures often cause seepage of the working fluid through a central conduit or tube's pores, even against capillary forces acting to retain the working fluid within the pores. The particle growth systems disclosed herein can facilitate the detection of very small hazardous airborne particles (e.g., those with a diameter less than 300-400 nm), for example, in industrial and/or occupational settings. These systems can sample air at rates in the range of a few milliliters to a few liters per minute and concentrate particulate matter into picoliter to milliliter liquid samples for subsequent on-line or off-line physical and/or chemical analysis.

Polymer Electrolyte Membranes

A PEM is a selectively permeable membrane that functions as a solid electrolyte or ionomer capable of conducting preselected targets, including individual protons, individual water molecules, and/or some individual alcohol molecules, while being impermeable to most gases (such as nitrogen, oxygen, or hydrogen) and bulk liquids. A preselected target can be transported across a PEM on an ion-by-ion or molecule-by-molecule basis. That is, individual target ions or individual target molecules can be transported one at a time across the PEM. For example, when a PEM forms a boundary between a body of liquid water and a body of gas, the PEM can inhibit the bulk water from flowing through the PEM into the gas, but still conduct individual ions and water molecules through the PEM into the gas. The transportation of the preselected targets across the membrane can be driven by an ionic or molecular gradient across the membrane.

A steady-state water permeation process through a PEM can include sorption of water into the membrane at a first side of the membrane, diffusion of water across the membrane, and desorption of water from the membrane at the second side of the membrane. See, e.g., *Diffusion and Interfacial Transport of Water in Nafion*, Zhao, et al., Journal of Physical Chemistry B, 2011, 115, 2717-2727, which is incorporated by reference herein in its entirety. Regardless of the mechanism, a PEM avoids bulk transfer of liquid through the membrane, as would occur with a porous substrate or walls used in most particle condensation growth systems.

One example of a PEM is a perfluorosulfonated ionomer (PFSI) membrane, for example a sulfonated tetrafluoroethylene based fluoropolymer-copolymer, such as NAFION (a registered trademark of E. I. du Pont de Nemours and Company). This family of membranes each comprises a perfluorosulfonated random copolymer with a tetrafluoroethylene backbone and perfluoroalkyl ether side chains terminated by sulfonic acid groups. Certain embodiments incorporate perfluorovinyl ether groups terminated with sulfonate groups incorporated into the tetrafluoroethylene backbone. Specific membranes include those sold under the names NAFION 112, NAFION 115, NAFION 117, NAFION 324, NAFION 424, NAFION 438, NAFION 1110, NAFION N551PW, NAFION NR-211, NAFION NR-212, NAFION XL, and NAFION HP. NAFION can have various chemical configurations and thus several names in the IUPAC system. For example, IUPAC names for NAFION include:

ethanesulfonyl fluoride, 2-[1-[difluoro-[(trifluoroethenyl) oxy]methyl]-1,2,2,2-tetrafluoroethoxy]-1,1,2,2,-tetra-fluoro-, with tetrafluoroethylene; and tetrafluoroethylene-perfluoro-3,6-dioxa-4-methyl-7-octene-sulfonic acid copolymer.

NAFION membranes can molecularly transport limited preselected targets from one surface of the membrane to another without bulk transfer of the targets through the membrane. According to Zhao, et al., "Nafion microphase separates into hydrophilic domains of sulfonic acid groups and absorbed water imbedded in a hydrophobic matrix of tetrafluoroethylene (TFE) and perfluoroalkyl ether (PFA). Water and protons are transported through the network of hydrophilic domains. The hydrophilic domains swell and restructure as water is absorbed into Nafion, which changes the effective diffusion coefficient."

NAFION can comprise a network of hydrophilic domains extending throughout a substantially hydrophobic matrix, wherein individual ions or molecules can be transported through the network of hydrophilic domains, e.g., from one surface of a NAFION membrane to an opposite surface of the NAFION membrane. Although the chemical basis of NAFION's superior water conductive properties remain a focus of research, proposed mechanisms of transport are a physical transport mechanism in which solvated protons are transported in clusters of water, for example as hydronium ($H_3O^+$) and Zundel ions ($H_5O_2^+$). An alternative explanation is the Grotthuss mechanism, in which formation and breaking of O—H bonds in water molecules lead to the rapid, net transport through the membrane. Adachi, *Proton exchange membrane fuel cells: water permeation through NAFION membranes*, Simon Fraser University dissertation, 2010. The transport of water associated with the transport of protons is termed the electro-osmotic drag, which differs substantially from the physical permeation of spatial voids in a membrane.

As shown in FIG. 8 of Zhao, et al., the hydrophilic domains of a PEM such as NAFION can have a width or diameter on the order of a width or diameter of a water molecule (e.g., less than 2 nm, or less than 1 nm, or less than 500 pm), such that at room temperature (25° C.) individual water molecules, or other similarly sized ions or molecules, can be transported through the hydrophilic domains, while larger molecules and bulk fluids cannot. This process is referred to herein as "molecular transport," and membranes that exhibit this behavior are referred to as "substantially impermeable" to the flow of bulk gases and liquids. "Porous," as used herein, refers to materials that are not substantially impermeable to bulk gases and liquids and allow the flow of bulk gases and/or liquids through one or more open pores, which can form a network of interconnected interstitial spaces within the membrane where liquid or gas can reside in the bulk form, and through which liquid or gas can flow in the bulk form.

In some cases, a NAFION membrane can have a hydrophilic volume fraction greater than about 0.1, greater than about 0.12, greater than about 0.15, and/or greater than about 0.2. In some cases, higher hydrophilic volume fractions can lead to better performance of the systems.

Table 2 of Zhao, et al., provides quantitative experimental measurements of water transport rates (permeation rates) across a particular non-limiting example of a NAFION membrane from a liquid at a first side of the NAFION membrane to a gas at a second side of the NAFION membrane. Specifically, at 30° C., the permeation rate was found to be 7.4 $\mu mol/cm^2/s$, at 50° C., the permeation rate was found to be 14 $\mu mol/cm^2/s$, at 70° C., the permeation rate was found to be 23 $\mu mol/cm^2/s$, and at 80° C., the permeation rate was found to be 28 $\mu mol/cm^2/s$. These quantities were found to be smaller than the rate of evaporation from a film of water by nearly a factor of $10^4$.

In certain specific examples of the embodiments disclosed herein, the PEM membrane allows a working fluid at 30° C. to permeate a NAFION membrane at a rate of less than about 8 $\mu mol/cm^2/s$, or at 50° C. at a rate of less than about 15 $\mu mol/cm^2/s$, or at 70° C. at a rate less than about 25 $\mu mol/cm^2/s$, or at 80° C. at a rate less than about 30 $\mu mol/cm^2/s$. Certain specific examples of the embodiments disclosed herein can be operable over a wide range of temperatures, such as between 30° C. and 80° C., and in some cases up to at least 150° C.

Systems disclosed herein can include PEMs such as perfluorosulfonated ionomer (PFSI) membranes, for example a sulfonated tetrafluoroethylene based fluoropolymer-copolymer, such as NAFION, or other membranes having properties similar to those of PEMs described herein, to allow selective molecular transport of a working fluid across the membrane and to prevent the bulk flow of liquids and/or gases through the membrane. These membranes can be particularly useful in the disclosed particle growth systems because they are substantially impermeable to gases and the bulk flow of liquid at 25° C., thus permitting a controlled movement of water molecules through the membrane and into the conduit or tube to encourage particle growth.

More particularly, PEMs such as NAFION are substantially impermeable to gases at pressures ranging from at least as small as 0.05 ATM to at least as high as 5 ATM. As specific examples, the permeability of dry NAFION 117 to $O_2$ is about 1.08 Barrer at STP, and the permeability of dry NAFION 117 to $N_2$ is about 0.26 Barrer at STP. Due to the molecular transport of individual molecules across PEMs, the permeability of a PEM to a gas is typically independent of the pressure of the gas at either side of the PEM, and is typically independent of any pressure gradient across the PEM.

Various non-porous, substantially impermeable polymer membrane materials are suitable for use as the PEM of the systems described herein. Examples include:
1. Sulfonated Tetrafluoroethylene
2. Sulfonated Polyether Ether Ketone
3. Phenylphosphonic Polyphosphazene
4. Sulfonated and Phosponated Polyaryloxyphosphazenes
5. Poly(ethylene oxide)-poly(butylene terephthalate)
6. The materials listed in Table 2 from Roziere and Jones, *Non-Fluorinated Polymer Materials for Proton Exchange Membrane Fuel Cells* (2003), Annu. Rev. Mater. Res., 33:503-55, doi: 10.1146/annurev.matsci.33.022702.154657). This Table 2 is hereby incorporated herein by reference in its entirety.
7. The materials listed in Table 1 from Smitha, et al., *Solid Polymer Electrolyte Membranes for Fuel Cell Applications—a Review* (2005), Journal of Membrane Science 259, 10-26. This Table 1 is hereby incorporated herein by reference in its entirety.

Example Particle Growth Systems

FIG. 1 shows one embodiment of an aerosol particle growth system 100. System 100 includes a cylindrical outer housing 104 having an internal reservoir containing a working fluid 106, a straight, cylindrical PEM tube 102 extending through the outer housing 104 and working fluid 106, and a cylindrical heater 108 disposed around the outer housing 104. The outer housing can comprise any suitable material, including steel, aluminum, brass, copper, etc. FIG. 1 also shows that, when the system 100 is in operation, a gas containing relatively small seed particles 110 (an aerosol) enters an inlet at a first end of the PEM tube 102, travels along the length of the PEM tube 102 through the outer housing 104, and exits an outlet at a second end of the PEM tube 102 containing relatively large particles 112 grown from the relatively small particles 110. In system 100, the working fluid (or condensing fluid) 106 in the reservoir comprises liquid water and the PEM tube 102 comprises a NAFION material. System 100 can also include a pump (not illustrated) to control the flow of the aerosol through the system 100. The pump can be coupled, for example, to the inlet at the first end of the PEM tube 102, or to the outlet at the second end of the PEM tube 102.

A method of using system 100 includes providing the system 100 in an environment to be studied. The heater 108 is used to heat the working fluid 106 in the reservoir inside the outer housing 104 to a temperature (e.g., 70° C.) higher than that of the environment to be studied (e.g., 25° C.). An aerosol from the environment to be studied is fed into the first end of the PEM tube 102 as the working fluid 106 is molecularly transported across the PEM into the PEM tube 102 and into the flow path of the aerosol. The particles in the aerosol act as nucleation sites for the gaseous working fluid 106 and the gaseous working fluid condenses onto the particles, thereby increasing the size of the particles.

Figure 2:
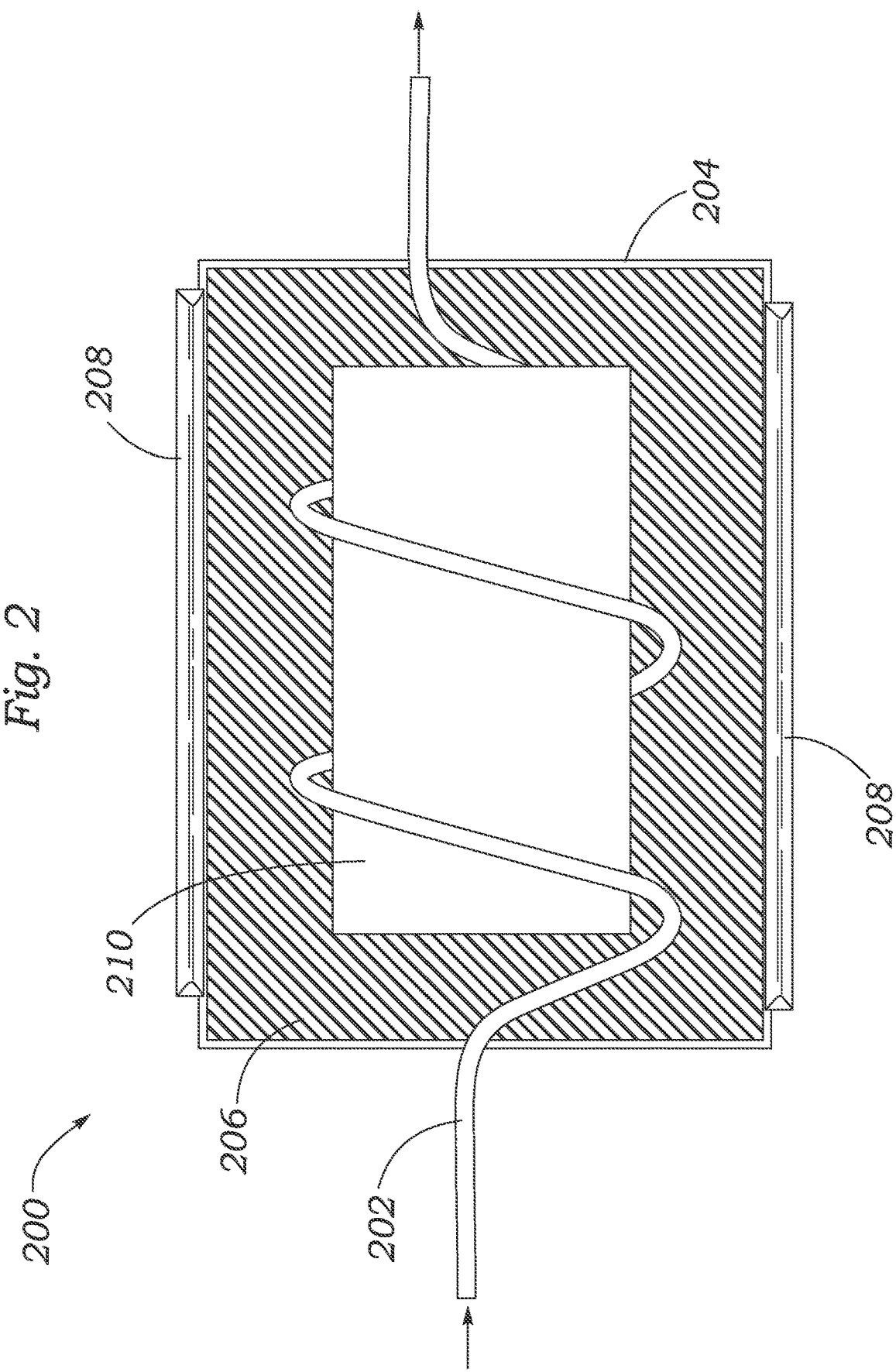
FIG. 2 is a schematic illustration of a second particle growth system including a coiled PEM tube.

FIG. 2 shows another embodiment of an aerosol particle growth system 200. System 200 includes a cylindrical outer housing 204 having an internal reservoir containing a working fluid 206, a coiled, generally helical PEM tube 202 extending through the outer housing 204 and working fluid 206, and a cylindrical heater 208 disposed around the outer housing 204. In some cases, the heater 208 (or any other heater described herein) can be a Peltier, thermoelectric, resistive electric, or inductive device. The helical or coiled PEM tube 202 can be coiled or wound around a cylindrical block of material 210 at the center of the outer housing 204. The helical PEM tube 202 can have a coil radius of any suitable dimension, such as about 0.25", 0.5", 1", 2", 5", or 10", can have an inside diameter of any suitable dimension, such as about 0.086 inches, and can have a length of any suitable dimension, such as about 1 inch.

The helical PEM tube 202 provides a longer flow path for an aerosol through the outer housing 204 than a straight tube through the outer housing 204 does, allowing the development of miniature systems. In some cases, helical PEM tube 202 can also generate secondary flows and promote increased mixing and higher saturation inside the tube. As a result, the helical PEM tube 202 allows an aerosol flowing through the tube to be heated to higher temperatures and higher saturation levels than a straight tube allows. When the system 200 is in operation, a gas containing relatively small particles enters an inlet at a first end of the helical PEM tube 202, travels along the length of the PEM tube 202 through the outer housing 204, and exits an outlet at a second end of the PEM tube 202 containing relatively large particles grown from the relatively small particles. In system 200, the working fluid (or condensing fluid) 206 in the reservoir comprises liquid water and the PEM tube 202 comprises a NAFION material. System 200 can also include a pump (not illustrated) to control the flow of the aerosol through the system 200. The pump can be coupled, for example, to the inlet at the first end of the PEM tube 202, or to the outlet at the second end of the PEM tube 202.

A method of using system 200 includes providing the system 200 in an environment to be studied. The heater 208 is used to heat the working fluid 206 in the reservoir inside the outer housing 204 to a temperature higher than that of the environment to be studied. An aerosol from the environment to be studied is fed into the first end of the PEM tube 202 (e.g., at a rate of about 1 liter per minute) as the working fluid 206 is molecularly transported across the PEM into the PEM tube 202 and into the flow path of the aerosol. The particles in the aerosol act as nucleation sites for the gaseous working fluid 206 and the gaseous working fluid condenses onto the particles, thereby increasing the size of the particles.

Figure 3:
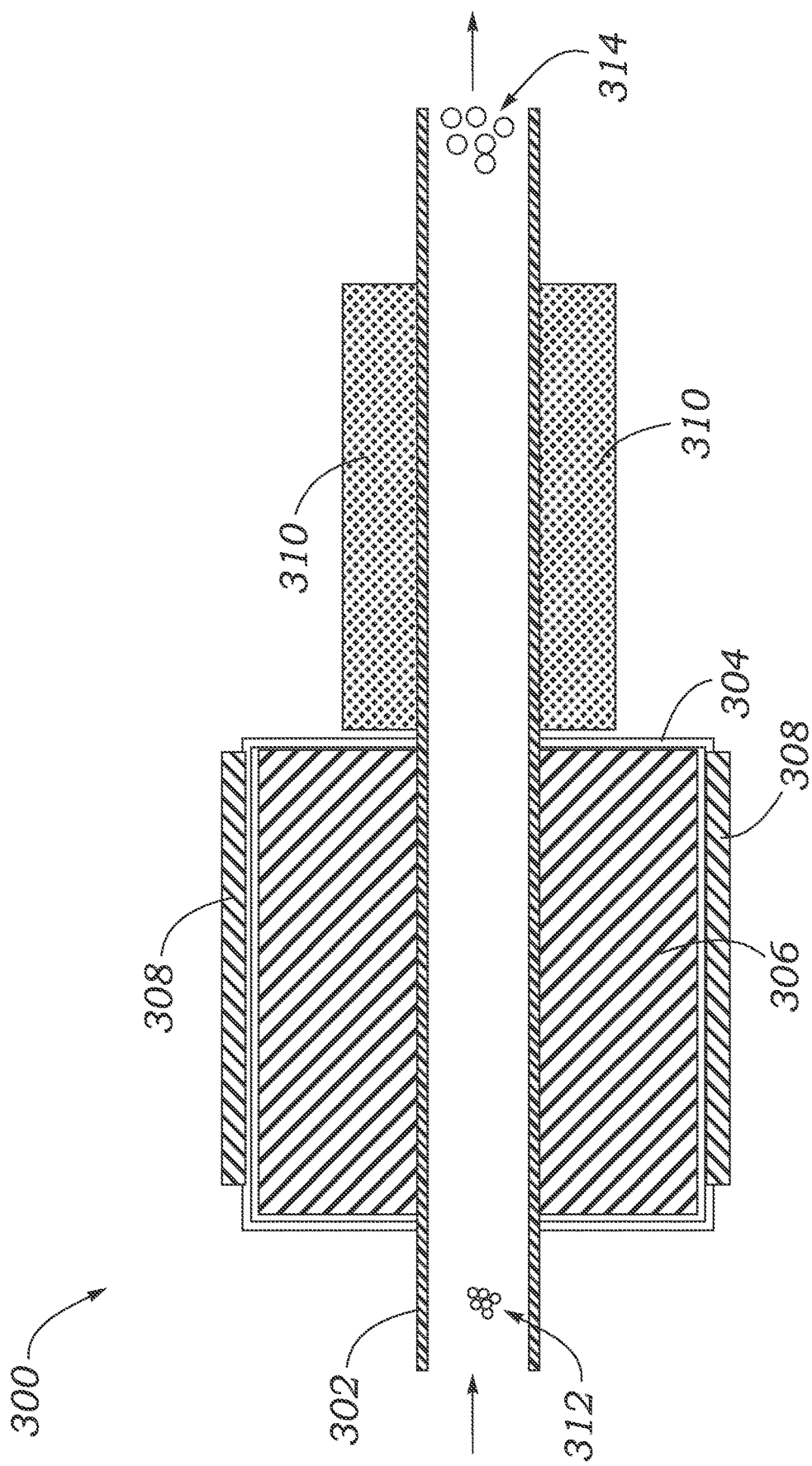
FIG. 3 is a schematic illustration of a third particle growth system including a straight PEM tube and a cooling device.

FIG. 3 shows another embodiment of an aerosol particle growth system 300. System 300 includes a cylindrical outer housing 304 having an internal reservoir containing a working fluid 306, a straight, cylindrical PEM tube 302 extending through the outer housing 304 and working fluid 306, and a cylindrical heater 308 disposed around the outer housing 304. FIG. 3 also shows that, when the system 300 is in operation, a gas containing relatively small particles 312 enters an inlet at a first end of the PEM tube 302, travels along the length of the PEM tube 302 through the outer housing 304, and exits an outlet at a second end of the PEM tube 302 containing relatively large particles 314 grown from the relatively small particles 312.

FIG. 3 also shows that the PEM tube 302 extends beyond an edge of the outer housing 304, and system 300 also includes a cooling device 310 disposed around the PEM tube 302 at a location displaced along the PEM tube 302 from the outer housing 304 and heater 308. The cooling device 310 can comprise one or more thermoelectric coolers, e.g., one or more Peltier coolers. The PEM tube 302, outer housing 304, heater 308, and cooling device 310 are arranged so that the outer housing 304 and heater 308 are located in the region of the first end of the PEM tube and the cooling device 310 is located in the region of the second end of the PEM tube. Thus, as the gas containing particles flows through the PEM tube 302, they encounter a relatively warm region first and a relatively cool region second. The PEM tube 302 can comprise a single tube of PEM material extending through both the heater 308 and the cooling device 310, or two separate tubes of material, a first extending through the heater 308 and the second extending through the cooling device 310. In system 300, the heater 308 can heat the working fluid 306 in the reservoir, and the heated working fluid can be transported across the PEM tube 302 into the aerosol flow path, which can become saturated with the vapors of the working fluid. The particle-containing flow, saturated with the working fluid, can then be cooled by the cooling device 310 and become supersaturated with the working fluid. In system 300, the working fluid (or condensing fluid) 306 in the reservoir comprises a liquid alcohol, such as isopropanol or n-butanol, capable of being transported molecularly across the PEM tube 302. System 300 can include a pump as described herein with regard to systems 100 and 200.

A method of using system 300 includes providing the system 300 in an environment to be studied. The heater 308 is used to heat the working fluid 306 in the reservoir inside the outer housing 304 to a temperature higher than that of the environment to be studied, e.g., to between about 40° C. and 50° C. The cooling device 310 is used to cool a region of the PEM tube 302 adjacent or near to the reservoir in the outer housing 304 to a temperature below that of the working fluid in the reservoir, or below that of the environment to be studied. An aerosol from the environment to be studied is fed into the first end of the PEM tube 302 as the working fluid 306 is molecularly transported across the PEM into the PEM tube 302 and into the flow path of the aerosol. The gaseous working fluid is carried by the flowing aerosol through the PEM tube 302 into the cooled region of the PEM tube 302, where the temperature of the aerosol decreases and the working fluid becomes supersaturated in the aerosol. The particles in the aerosol act as nucleation sites for the supersaturated gaseous working fluid 306 and the gaseous working fluid condenses onto the particles, thereby increasing the size of the particles.

Figure 4:
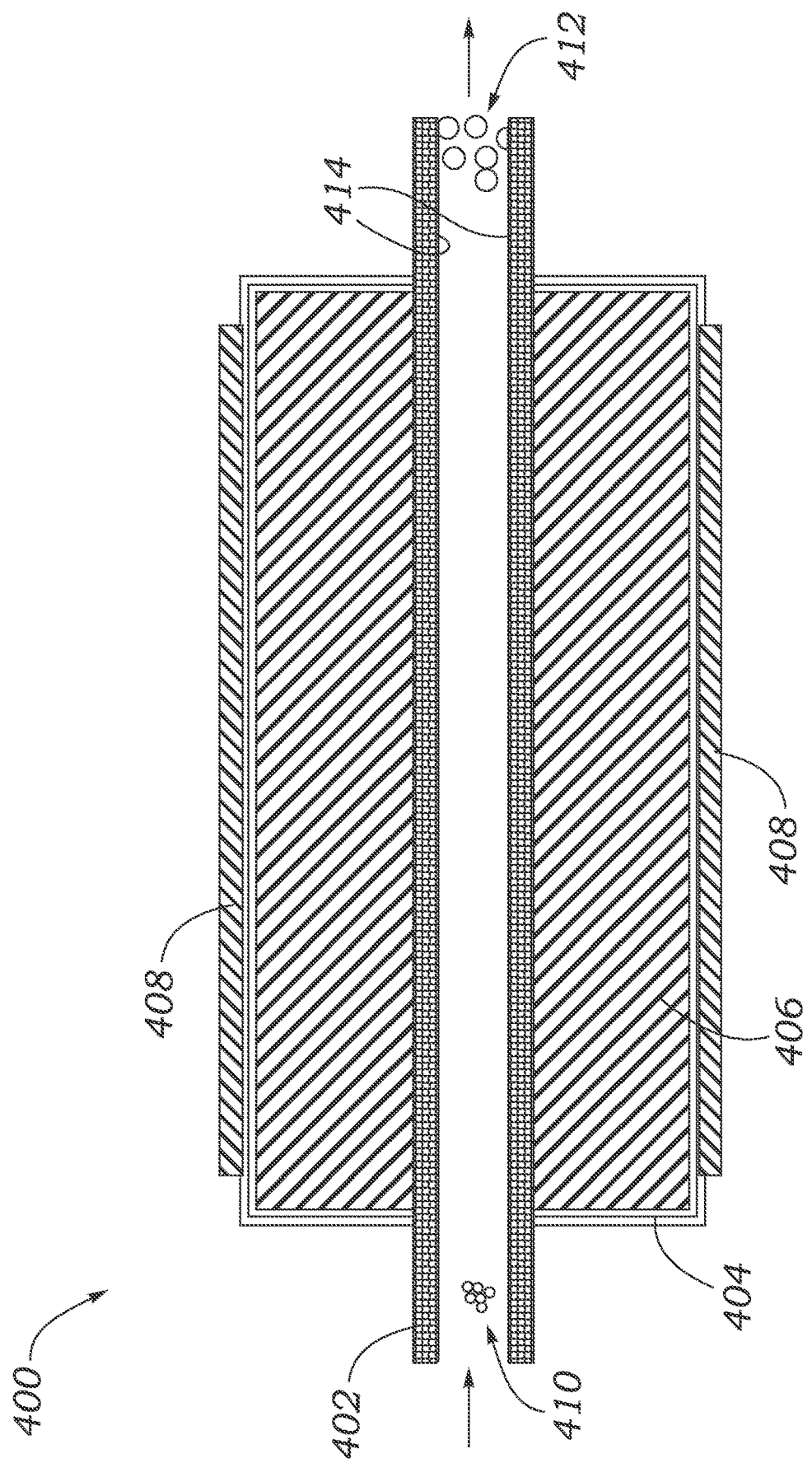
FIG. 4 is a schematic illustration of a fourth particle growth system including a composite tube comprising a rigid porous tube impregnated or coated with a PEM material.

FIG. 4 shows another embodiment of an aerosol particle growth system 400. System 400 includes a cylindrical outer housing 404 having an internal reservoir containing a working fluid 406, a straight, cylindrical porous or perforated tube or screen 402 extending through the outer housing 404 and working fluid 406, and a cylindrical heater 408 disposed around the outer housing 404. The porous tube 402 can be made of any suitable material such as a porous plastic, a porous metal, a sintered metal, etc. The porous tube 402 can be impregnated with a PEM material, such that the PEM material covers or fills its pores, or coated with a PEM material, or an inner PEM tube can be mounted to an internal surface of the porous tube 402, or an outer PEM tube can be mounted to an external surface of the porous tube 402, such that in any of these cases, a composite tube comprises a PEM tube 414 formed on a surface or surfaces of the porous tube 402.

In system 400, the porous tube 402 can comprise a relatively rigid material and provide structure, support, and rigidity to the PEM tube 414. Because the tube 402 is porous, the working fluid 406 can readily pass through the porous tube 402 and thus the porous tube 402 does not otherwise affect the function of the system 400. Impregnation or coating of the porous tube 402 can be accomplished by dipping the tube 402 into a PEM solution, by spraying a PEM onto the tube 402, etc. FIG. 4 also shows that, when the system 400 is in operation, a gas containing relatively small particles 410 enters an inlet at a first end of the porous tube 402 and inner PEM tube 414, travels along the length of the tubes 402 and 414, and exits an outlet at a second end of the porous and inner PEM tubes 402, 414, containing relatively large particles 412 grown from the relatively small particles 410. In system 400, the working fluid (or condensing fluid) 406 in the reservoir comprises liquid water or liquid alcohol and the PEM tube 414 comprises a NAFION material. In some embodiments, a particle growth system including a porous tube can be modified by coating the porous walls of the tube with a PEM to form a composite tube such as that shown in FIG. 4 and described herein. System 400 can include a pump as described herein with regard to systems 100 and 200.

A method of using system 400 includes providing the system 400 in an environment to be studied. The heater 408 is used to heat the working fluid 406 in the reservoir inside the outer housing 404 to a temperature higher than that of the environment to be studied. An aerosol from the environment to be studied is fed into the first end of the porous and PEM tubes 402, 414 as the working fluid 406 is molecularly transported through the porous tube 402 and across the PEM into the PEM tube 402 and into the flow path of the aerosol. The particles in the aerosol act as nucleation sites for the gaseous working fluid 406 and the gaseous working fluid condenses onto the particles, thereby increasing the size of the particles.

Figure 5:
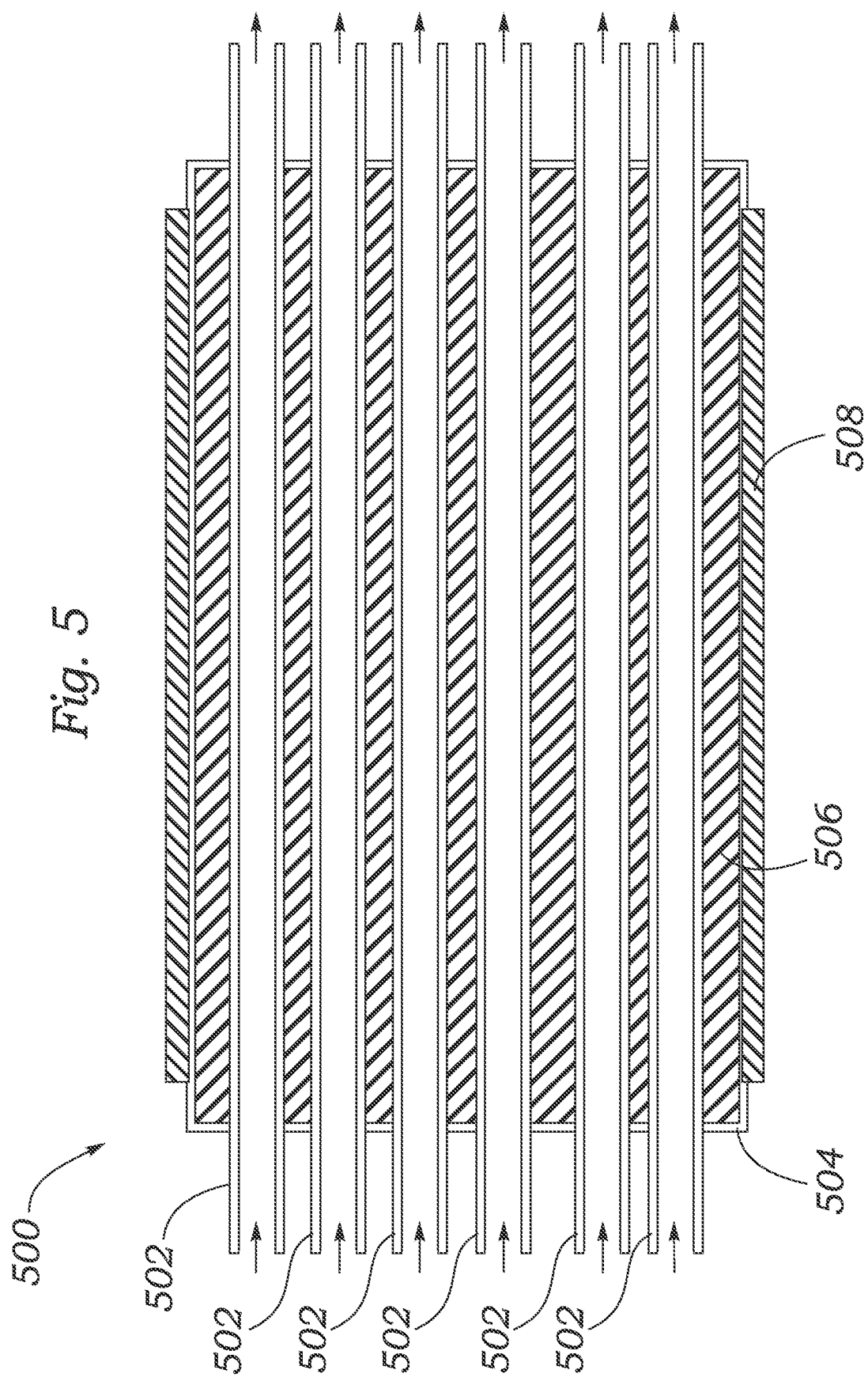
FIG. 5 is a schematic illustration of a fifth particle growth system including an array of PEM tubes.

FIG. 5 shows another embodiment of an aerosol particle growth system 500. System 500 includes a cylindrical outer housing 504 having an internal reservoir containing a working fluid 506, and an array of six straight, cylindrical PEM tubes 502 extending through the outer housing 504 and working fluid 506, and a cylindrical heater 508 disposed around the outer housing 504. FIG. 5 also shows that, when the system 500 is in operation, a gas containing relatively small particles enters an inlet at a first end of the PEM tubes 502, travels along the length of the PEM tubes 502 through the outer housing 504, and exits an outlet at a second end of the PEM tubes 502 containing relatively large particles. While six PEM tubes are used in the embodiment shown in FIG. 5, in alternative embodiments, any suitable number of PEM tubes can be used, for example, 2, 3, 4, 5, 6, 7, 8, 9, 10, 12, 15, 20, or more PEM tubes can be used.

In some embodiments, the aerosol flowing through each of the PEM tubes 502 can be the same. In other embodiments, different aerosols (with similar or dissimilar properties) can flow through different of the PEM tubes 502. In system 500, each of the PEM tubes 502 extends through a single reservoir and working fluid 506 within the outer housing 504. In alternative embodiments, the PEM tubes 502 can extend through different, distinct reservoirs formed in the outer housing 504. In some specific embodiments, one or more first reservoirs formed in the outer housing contain a first working fluid and one or more second reservoirs contain a second working fluid, wherein the first working fluid is not the same as the second working fluid. In other specific embodiments, all of the different, distinct reservoirs can contain the same working fluid. In some cases, two or more of the PEM tubes 502 can be coupled to one another to increase the length of an aerosol flow path through the system 500.

The array of PEM tubes 502 substantially increases the aerosol flow through (e.g., the throughput of) the system 500 (e.g., as compared to that for system 100). Further, by using an array of PEM tubes 502 within a single outer housing 504, the system 500 can be made smaller than other systems having similar capabilities, such as other systems capable of sampling multiple different, distinct aerosols. In system 500, the working fluid (or condensing fluid) 506 in the reservoir comprises liquid water or liquid alcohol and the PEM tubes 502 comprise a NAFION material. System 500 can include a respective pump for each of the PEM tubes 502, as described herein with regard to systems 100 and 200.

A method of using system 500 includes providing the system 500 in an environment to be studied. The heater 508 is used to heat the working fluid 506 in the reservoir inside the outer housing 504 to a temperature higher than that of the environment to be studied. An aerosol from the environment to be studied is fed into the first end of each of the PEM tubes 502 as the working fluid 506 is molecularly transported across the PEM into the PEM tube 502 and into the flow path of the aerosol. The particles in the aerosol act as nucleation sites for the working fluid 506 and the gaseous working fluid condenses onto the particles, thereby increasing the size of the particles.

Figure 6:
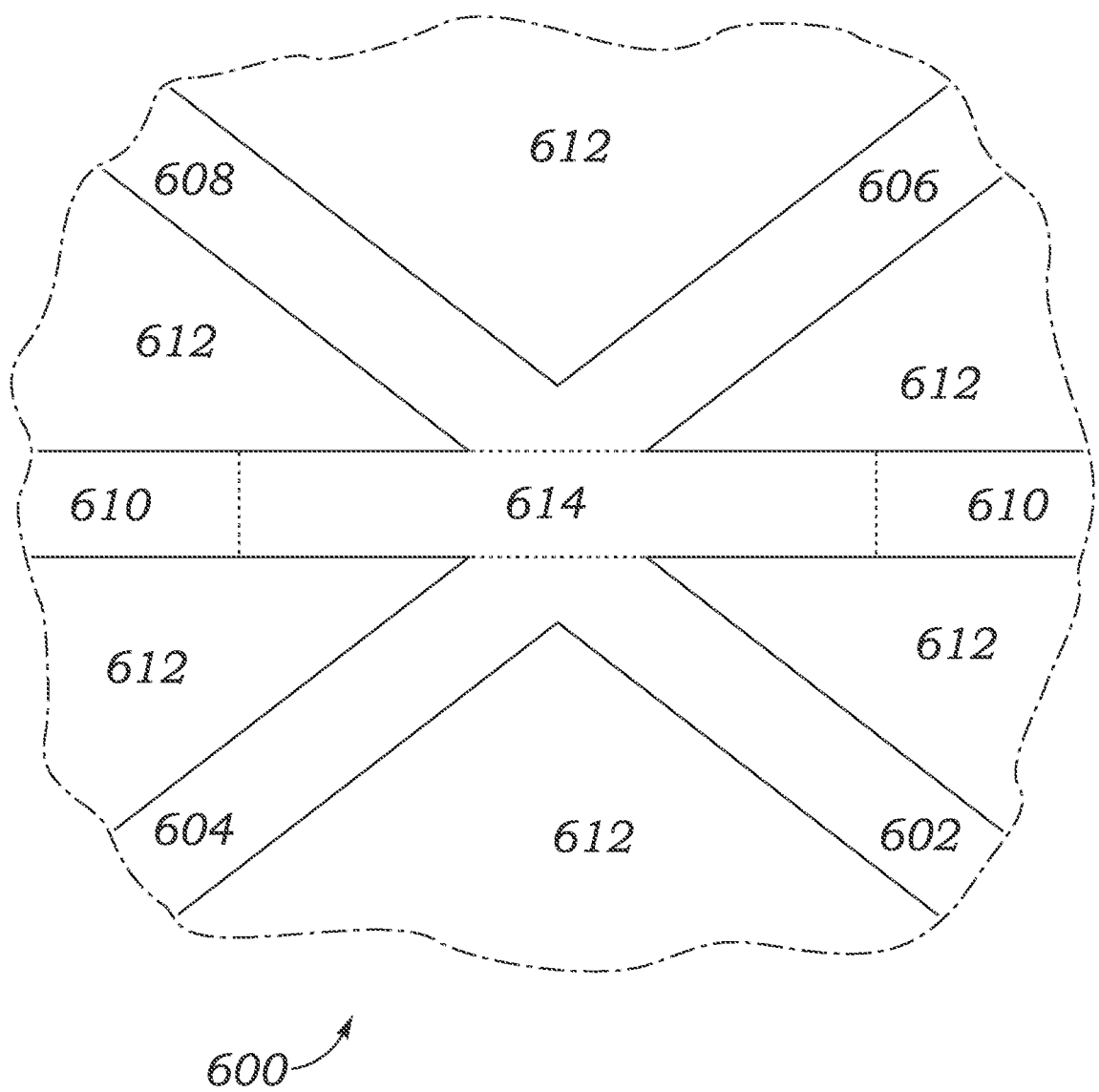
FIG. 6 is a schematic illustration of a sixth particle growth system including microfabricated channel structures and a PEM material.

FIG. 6 shows another embodiment of an aerosol particle growth system 600. System 600 includes a microfabricated PDMS mold 612 with a plurality of microfluidic channels 602, 604, 606, 608, and 610 formed therein. A PEM portion 614 (e.g., comprising NAFION) is provided within the channel 610 to separate the channels 602 and 604 from the channels 606 and 608. A working fluid is provided in the channels 602 and 604, for example, flowing from an inlet toward the PEM portion 614 through channel 602 and toward an outlet away from the PEM portion 614 through channel 604. An aerosol can flow through channels 606 and 608, for example, flowing from an inlet toward the PEM portion 614 through channel 608 and toward an outlet away from the PEM portion 614 through channel 606.

The working fluid can be molecularly transported across the PEM portion 614 from the channels 602 and 604 to channels 606 and 608, where the working fluid in a gaseous form can condense onto the particles of the aerosol flowing through the channels 606 and 608. A method of using system 600 includes providing the system 600 in an environment to be studied. An aerosol from the environment to be studied is fed into channel 608 as the working fluid is molecularly transported across the PEM portion 614 into the channels 606 and 608 and into the flow path of the aerosol. The temperature of the channel 606 and/or the channel 608 can be controlled to create supersaturation in the aerosol, as described herein. The particles in the aerosol act as nucleation sites for the gaseous working fluid and the gaseous working fluid condenses onto the particles, thereby increasing the size of the particles through condensation.

Figure 7:
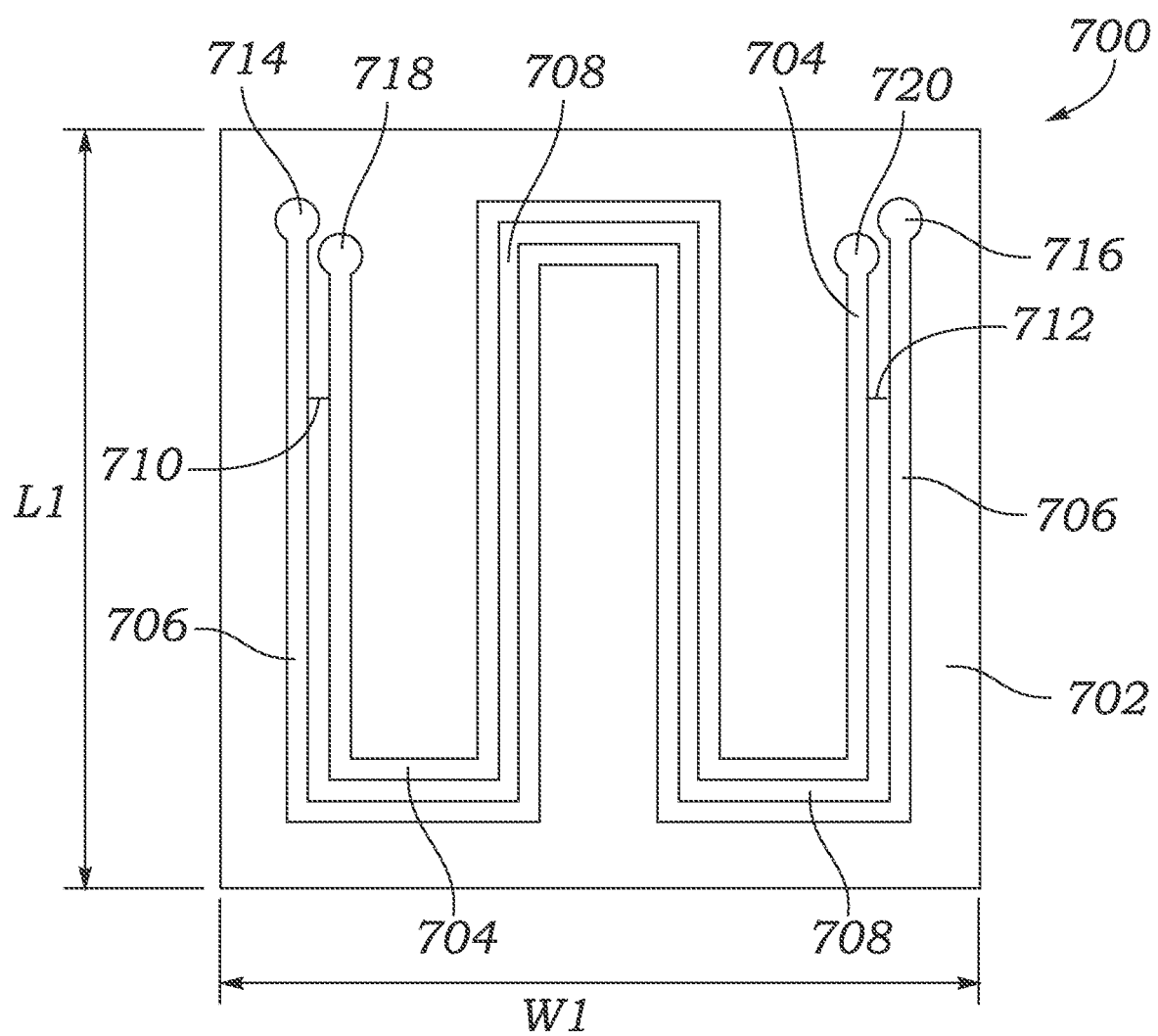
FIG. 7 is a schematic illustration of a seventh particle growth system including microfabricated channel structures and a PEM material.
Figure 9:
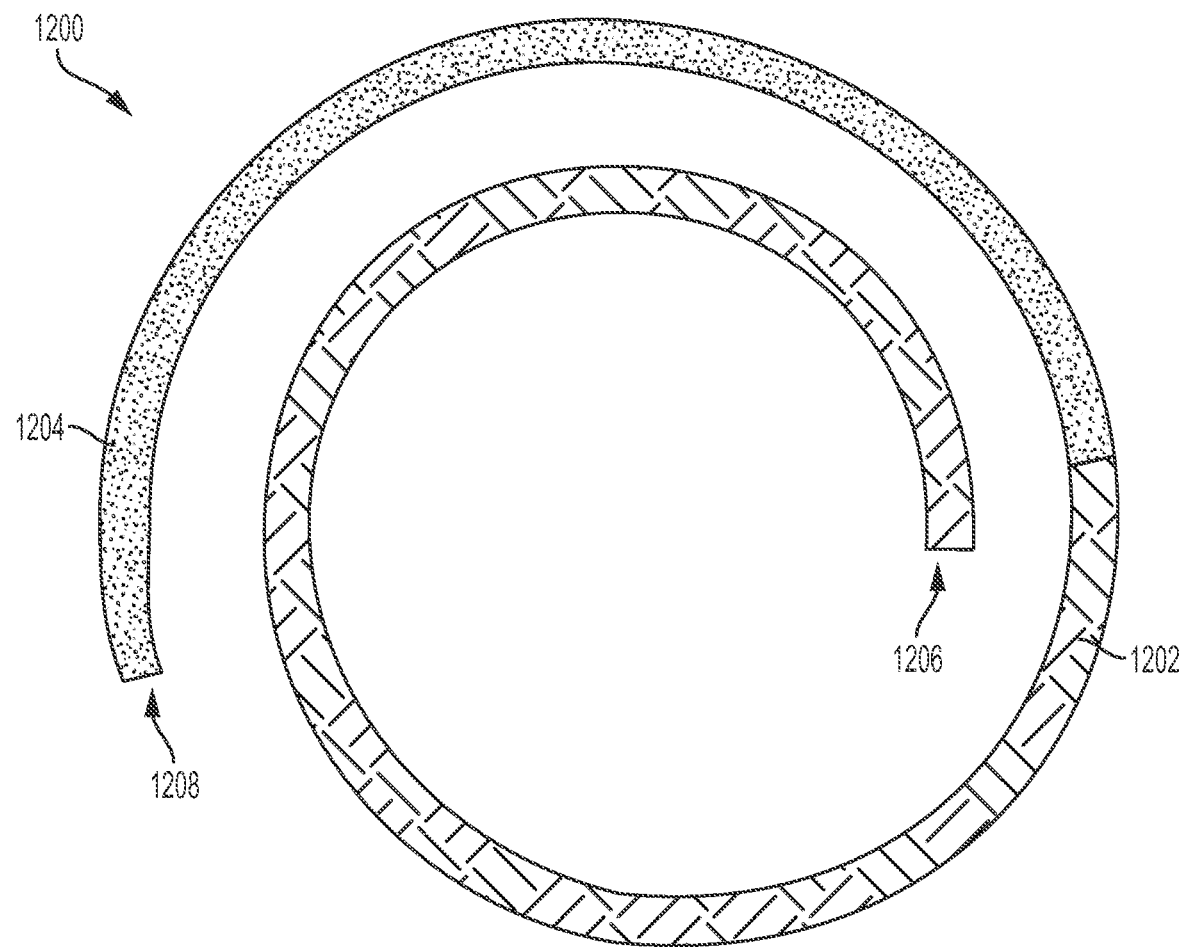
FIG. 9 illustrates a coiled tube including a first, relatively hot portion and a second, relatively cold portion.

Other configurations of microfabricated fluidic structures including PEMs can be used. For example, in some embodiments, the walls of microfabricated structures can be coated with a PEM or can be fabricated from a PEM. The PEM can separate a chamber or channel containing a working fluid from an aerosol flow path or an aerosol particle growth chamber. FIG. 7 shows another embodiment of an aerosol particle growth system 700. System 700 includes a microfabricated PDMS mold 702 with microfluidic channels 704 and 706 formed therein. The channels 704 and 706 can form extended, convoluted flow paths through the PDMS mold 702 to provide longer flow paths through the PDMS mold 702. A PEM portion 708 can extend from a first location 710 to a second location 712 and can be positioned to separate the channel 704 from the channel 706.

The PDMS mold 702, channels 704 and 706, and PEM portion 708 can be situated on a substrate of glass or similar material and can be covered with a coversheet of glass or similar material to substantially enclose the channels 704 and 706. The coversheet can have openings at locations 714, 716, 718, and 720 to allow access to the channels 704 and 706. The system 700 can have an overall length L1 of about one inch and an overall width W1 of about one inch, or can have larger or smaller dimensions. The system 600 and/or the system 700 can be fabricated according to any of various micro-fabrication techniques. In some cases, the system 600 and/or the system 700 can be fabricated using injection molding techniques.

A method of using the system 700 includes introducing an aerosol into channel 706 at an inlet at location 714, and allowing the aerosol to flow through the channel 706 and out of the channel 706 at an outlet at location 716. A working fluid is introduced into channel 704 at an inlet at location 718, and allowed to flow through the channel 704 and out of channel 704 at an outlet at location 720. In alternative embodiments, the working fluid is contained within channel 704 but does not flow through the channel 704. The working fluid is molecularly transported across the PEM portion 708 and into the flow path of the aerosol. The particles in the aerosol act as nucleation sites for the gaseous working fluid and the gaseous working fluid condenses onto the particles, thereby increasing the size of the particles. Temperature of the flow can be controlled, as described elsewhere herein, to create supersaturation in the aerosol, leading to condensational growth of the particles. In some cases, system 600 and/or system 700 can include one or more pumps for controlling the flow of an aerosol through the respective microfluidic channels, as described herein with regard to systems 100 and 200.

Exemplary methods of increasing the size of particles in an aerosol can include rapidly, turbulently, and adiabatically mixing a first aerosol flow with a second aerosol flow. The first aerosol flow is supersaturated, or saturated, or substantially saturated with vapors of a working fluid, and/or has a relative humidity of about 100%, and is at a first, relatively high temperature. The second aerosol is substantially unsaturated, substantially dry, substantially saturated, and/or has a relative humidity substantially less than that of the first aerosol, and is at a second, relatively low temperature. In some embodiments, such a mixing process can result in an aerosol supersaturated with a gaseous working fluid by rapidly lowering the temperature of the first aerosol flow. In some embodiments, a particle growth system can comprise one or more PEMs and be configured to rapidly and turbulently mix first and second aerosols such as the first and second aerosols described herein.

FIG. 8 illustrates an exemplary method 800 of using a particle growth system including a PEM. At 802, the method includes providing a particle growth system having first and second chambers. At 804, the method includes introducing a working fluid into the first chamber. At 806, the method includes introducing an aerosol into the second chamber, which is separated from the first chamber by a PEM. At 808, the method includes heating a first portion of the second chamber. At 810, the method includes cooling a second portion of the second chamber. In embodiments in which the second chamber is a flow channel through which the aerosol flows, the heated first portion of the second chamber can be before the cooled second portion of the second chamber along the flow path of the aerosol. At 812, the method includes allowing the working fluid to be molecularly transported across the PEM into the second chamber. At 814, the method includes allowing the working fluid to condense onto aerosol particles in the second chamber. At 816, the method includes detecting, collecting, or studying the aerosol particles.

Variations in Flow Characteristics, Heating and Cooling, and Working Fluids

Many variations of the described embodiments are possible. In some cases, an aerosol can flow through a PEM tube or a microfluidic channel of an aerosol particle growth system laminarly or turbulently. For example, a pump can be coupled to the aerosol particle growth system to control the flow of the aerosol through the system, and the pump can control the speed of the aerosol flow through the system, so as to force the aerosol to flow either laminarly or turbulently through the system. In some cases, agitation of the aerosol caused by the turbulent flow can help to condense a working fluid in the aerosol onto particles in the aerosol and thereby increase the size of the particles. Such systems employing turbulent aerosol flow through a single PEM tube or microfluidic channel can be advantageous over the rapid and turbulent mixing of two aerosol flows, as described herein, in part because these systems do not require the mixing of two different aerosol flows and are therefore simpler.

In some cases, the temperature(s) of one or more portions of a PEM tube or a microfluidic channel of an aerosol particle growth system can be controlled. In some cases, a first portion of a PEM tube or a microfluidic channel closer to the inlet than to the outlet can be heated so as to be warmer than a second portion of the PEM tube or the microfluidic channel closer to the outlet than to the inlet. In other cases, the second portion can be heated so as to be warmer than the first portion. Such an embodiment can be particularly advantageous when used in combination with water as the working fluid, as water has a higher mass diffusivity than the thermal diffusivity of air, which can lead to improved supersaturation. In some cases, the difference in temperature between two portions of a PEM tube can be at least 5° C., or between 5° C. and 35° C., or at least 35° C. In some cases, the working fluid of an aerosol particle growth system can be water. In other cases, the working fluid can be an alcohol or other desirable condensate that can transport through the PEM. In some cases, a PEM tube of an aerosol particle growth system can be straight, curved, coiled, or helical. Any of the particle growth systems described herein can be modified so as to employ laminar or turbulent flow as described herein, the various configurations of heating and cooling schemes described herein, the various working fluids described herein, and/or PEM tubes having the shapes described herein.

As one example, FIG. 9 illustrates a coiled tube 1200 which includes a heated or relatively hot portion 1202 in which an aerosol can become saturated with a working fluid and a cooled or relatively cold portion 1204 in which the aerosol can condense onto particles in the aerosol. The aerosol can enter the tube 1200 with relatively small particles at an inlet 1206, flow through the tube 1200, and exit the tube 1200 with relatively large particles at an outlet 1208. The aerosol can flow turbulently through the tube 1200, and the tube 1200 can be surrounded by a working fluid (not illustrated) which can comprise water or an alcohol.

As another example, a coiled tube can have a coil radius of 0.5 inches, an inside diameter of 0.086 inches, and a length of 1.0 inches. The coiled tube can be surrounded by water at 70° C., and an aerosol at 25° C. and 1.0 saturation ratio (100% relative humidity) can enter the coiled tube at a rate of 1.0 liter per minute.

Example Applications

Particle growth systems such as those described herein can be used in various ways to help detect, collect, and/or analyze airborne particles. In one example, as an aerosol exits a particle growth system, such as one of the particle growth systems described herein, the aerosol can enter a particle collection system such as a collection system using an inertial (e.g., an impaction) or electrical mechanism to collect the grown particles for subsequent analysis. The aerosol particles can be pre-concentrated into small volumes of liquid for later on-line or off-line chemical and/or physical analyses of the particulate matter, e.g., microscopy, chemical analysis, protein analysis, etc.

In another embodiment, as an aerosol exits a particle growth system, the aerosol can enter an optical particle detection or counting system, where the particles can be detected and/or counted. For example, the aerosol can enter a laser particle counter that counts interruptions in laser beams caused by passing particles using a photodetector such as a photodiode. Because the particles exiting the particle growth system are larger than those in the ambient atmosphere (i.e., those entering the particle growth system), they are easier to reliably detect and/or count. For example, some laser particle counters are unable to reliably count particles less than about 300-400 nm in diameter. Thus, the particle growth systems described herein can be particularly advantageous in the detection and counting of particles smaller than 300-400 nm in diameter. Such an embodiment can be referred to as a condensation particle counter ("CPC") and can be used as part of a mobility spectrometer. Such a counting system can be employed to measure a particle size distribution of the aerosol using mobility and other techniques.

Exemplary Helical Growth Systems

Growing particles by exposing them to a supersaturated vapor is a widely used technique employed for sampling, detecting, and quantifying particle concentrations. Condensation particle counters, based on this principle, are highly sensitive particle detectors that can be employed for a wide range of applications from field studies investigating atmospheric new particle formation to monitoring occupational safety conditions. Collecting grown particles provides the opportunity for further physico-chemical analysis. Portable particle samplers and detectors can be desirable for spatial resolution of particle properties and behavior in atmospheric and occupational health contexts. Desirable portable instruments are cheap, light-weight, easily maintained. One challenge in miniaturizing condensation based particle samplers is retaining enough residence times while minimizing overall instrument dimensions.

Laminar flow based particle detectors and samplers create supersaturation required for condensational growth by exposing a gas stream saturated with the working fluid to a growth tube held at a different temperature. Simultaneous transport of heat and working fluid vapor transport take place in the growth tube. Both phenomena are dominated by parallel physical phenomena, namely convective transport in the axial direction and diffusive transport in the radial direction. Supersaturation is created by the interplay of these simultaneous transport phenomena and the relative importance of the phenomena strongly dominate the saturation ratios achieved. The weightage of diffusive heat transport to mass transport is characterized by the dimensionless group Lewis number, Le, which is a ratio of the thermal diffusivity of the gas to the diffusivity of the working fluid vapor in the gas. Ideally, higher saturation ratios are desired in the inner regions of the growth tube to help grow the smallest particles possible before they are diffusively lost to the walls. Commonly used butanol CPC's, where $Le>1$, achieve this by cooling a gas stream saturated with vapor in the growth tube.

Water based particle samplers and detectors offer relative safety compared to condensation growth devices that use organic compounds as the working fluid. However, in contrast with butanol CPC's, water CPC's can operate under $Le<1$. Thus, the conductive transport of heat can be slower than the diffusive transport of water vapor in the radial direction. In such conditions, water would be depleted faster than heat from the inner regions of the tube, leaving higher saturation ratio near the tube walls where it is less desirable. One feature of water CPC's are the porous walls in the growth tube that provide an inward flux of water vapor which confines higher saturation ratios to the desirable inner regions. These growth tubes can operate with the saturator temperature lower than the condenser/growth tube temperature in contrast with growth tubes employing organic working fluids. Water based condensation growth tubes can be considered to be devices that create supersaturation by the gentlest possible mixing of two different gas streams, unlike devices that achieve the same result by turbulent mixing of gas streams saturated with vapor at different temperatures.

Described below are simulations and resulting data for generally helical, water-based growth tube embodiments, such as those that can be used for miniaturized personal instrumentation. The disclosed water-based growth tubes can include a coiled, generally helical water-permeable NAFION tube. The coiled flow path helps in confining a longer tube into an instrument of smaller dimensions while providing sufficient residence time for particles to grow.

The saturator where the sampled aerosol flow is presaturated and the condenser where particles are grown can both comprise generally helical NAFION tubes housed in chambers containing the working fluid, e.g., water. The saturator chamber temperature can be held below the condenser temperature. Simulations described below demonstrate the generation of saturated regions in the growth tube, model the growth of particles along their flow paths, and characterize particle loss in the helical tubes.

Transport calculations, which include laminar flow equations and simultaneous heat and mass transport (of water vapor) equations, were solved for a helical growth tube using the commercial simulation package COMSOL 5.0. The transport equations below are depicted in their scaled form along with boundary conditions and material properties. One significant difference from other growth tube calculations is the use of flux boundary conditions for water vapor transport at the growth tube walls in contrast with a specification of vapor saturation at the walls. Mass transfer coefficients are used for water transport across the NAFION membrane, which are empirically determined in the temperature range from 303 to 353 K.

NAFION tube diameter was chosen as about 2 mm, though various other tube diameters can be used analogously. The growth tube temperature did not exceed 353 K as NAFION is known to dehydrate and lose its permeability to water around this temperature. The radius and pitch of the helical coil was also restricted to values reasonable enough to achieve aspect ratios sufficient for miniaturization and avoid flow obstructions in the tube due to pinching when wound too tightly. Flow rates were varied in the range 5 to 100 mL/min and calculations of Reynolds numbers place the flow conditions in the laminar regime for helical tubes.

Particle trajectory calculations were also computed to estimate particle losses in the helical tube at different flow and helix geometry conditions. Newton's laws of motion were solved for particles of various sizes (1 to 5 μm) with their densities assumed to be that of bulk water. The only external force considered on the particle was the viscous drag force computed from a Stokes model. These calculations were done to quantify the relative importance of inertial (here centrifugal) and drag forces and their role in the loss of grown particles.

The growth of particles in the growth tube is modeled by simple models characterizing volumetric growth from a balance of condensation and evaporation. Both condensation and evaporation processes are described by collision rates between the particle and the vapor molecules. Growth is assumed to occur once particles experience the required Kelvin critical saturation ratio in their paths. Focus was on on growing and detecting small particles (<100 nm) so that inertia neglected equations of motion apply for the particles. Diffusion of particles was neglected to simplify the growth model and understand the maximal growth possible. Hence, in this approximated picture of particle motion and growth, particles follow the laminar flow stream lines and grow along them.

Scaled Transport Equations:

$$\nabla^*\cdot(\rho^* u^*)=0 \tag{1}$$

$$\rho^*(u^*\cdot\nabla^*)u^*=\nabla^*\cdot(-p^*I+\mu^*(\nabla^*u^*+(\nabla^*u^*)^T)) \tag{2}$$

$$\rho^* C_p^* u^*\cdot\nabla^*\theta=\nabla^*\cdot(k^*\nabla^*\theta) \tag{3}$$

$$u^*\cdot\nabla^*c^*=\nabla^*\cdot(D^*\nabla^*c^*) \tag{4}$$

where the operators and quantities with * in the superscript are scaled relative to inlet quantities and/or typical scales (average speed for velocity, diameter for length etc.)

Specifically, $$p^* = \frac{p}{\rho_{in} U_{av}^2} \tag{5}$$

$$\theta = \frac{T - T_{in}}{T_{wall} - T_{in}} \tag{6}$$

$$c^* = \frac{c - c_{in}}{c_{sat}(T_{wall}) - c_{in}} \tag{7}$$

$$\rho^* = \frac{T_{in}}{T} \tag{8}$$

$$C_p^* = \frac{c_p}{c_{p,in}} \tag{9}$$

$$\mu^* = \frac{1}{Re_{in}} \frac{\mu}{\mu_{in}} \tag{10}$$

$$k^* = \frac{1}{Re_{in} Pr_{in}} \frac{k}{k_{in}} \tag{11}$$

$$D^* = \frac{1}{Re_{in} Pr_{in} Le_{in}} \frac{D}{D_{in}} \tag{12}$$

Boundary Conditions:

Flow: Volumetric flow rate of the gas is varied from ~5 to 100 mL/min. No slip conditions are used at the growth tube wall. Pressure at outlet set to atmospheric pressure.

Heat transport: Inlet temperature $T_{in}$ of the gas entering the growth tube is set to the saturator temperature. The wall of the growth tube $T_{wall}$ is set to the condensor temperature.

Water transport: The gas entering the helical growth tube is assumed to be saturated at the temperature of saturator.

At the wall, two boundary conditions are employed representing limits, namely a mass flux condition based on NAFION mass transfer coefficients from Zhao et al. (2011) or a specification of water vapor saturation at the condenser walls. A first boundary condition, B.C. 1, is as follows:

$$-n\cdot N_{water}^* = K^*(1-S|_{wall}) \tag{B.C. 1}$$

where $S|_{wall}$ is the saturation ratio at the wall, K* is the (Zhao et al., 2011) mass transfer coefficient and $-n\cdot N_{water}^*$ denotes the flux of water vapor into the growth tube wall at the location where the outward unit normal is $n\cdot 1-S|_{wall}$ is the mass transfer driving force in terms of water activities. The activity of pure water is unity, while the saturation ratio is the water vapor activity in the gas phase. It is noteworthy that K* is a lumped mass transfer coefficient measured for driving force differences in terms of bulk values, and not strictly in terms of interfacial values as described in B.C. 1 above. Therefore, this boundary condition may be considered to be a limiting case. Some reports indicate that NAFION surface is dominated by hydrophobic domains when contacted with water vapor saturated gas (e.g., Bass, Berman, Singh, Konovalov, & Freger, 2010).

The second limiting case is the assumption of water saturation at wall temperatures on the condenser wall. This will be referred to as the second boundary condition, B.C. 2. This limit is approached when the NAFION membrane sufficiently swells up by water uptake into its hydrophilic domain even when contacted with gas on one side. This limit is readily reached on the liquid water-membrane interface of the condenser.

Material Properties:

Air (79% nitrogen, 21% oxygen on a molar basis) properties are described as a function of temperature as:

$$C_p = \frac{0.79 \frac{C_{p,N_2}}{M_{N_2}} + 0.21 \frac{C_{p,O_2}}{M_{O_2}}}{M_{air}} \quad (13)$$

$$\mu = \sum_{\alpha=N_2,O_2} \frac{x_\alpha \mu_\alpha}{\Sigma_\beta x_\beta \varphi_{\alpha\beta}} \quad (14)$$

$$k = \sum_{\alpha=N_2,O_2} \frac{x_\alpha k_\alpha}{\Sigma_\beta x_\beta \varphi_{\alpha\beta}} \quad (15)$$

where $$\varphi_{\alpha\beta} = \frac{1}{\sqrt{8}} \left(1 + \frac{M_\alpha}{M_\beta}\right)^{-1/2} \left[1 + \left(\frac{\mu_\alpha}{\mu_\beta}\right)\left(\frac{M_\beta}{M_\alpha}\right)^{1/4}\right]^2 \quad (16)$$

The following models are used for pure substance properties and diffusion coefficient of water in air:

$$C_{p,N_2} = \frac{28.98641 + 1.853978\left(\frac{T}{1000}\right) - 9.647459\left(\frac{T}{1000}\right)^2 + 16.63537\left(\frac{T}{1000}\right)^3 + 0.000117\left(\frac{1000}{T}\right)^2}{M_{N_2}} \quad (17)$$

$$C_{p,O_2} = \frac{31.32234 - 20.23531\left(\frac{T}{1000}\right) + 57.86644\left(\frac{T}{1000}\right)^2 - 36.50624\left(\frac{T}{1000}\right)^3 - 0.007374\left(\frac{1000}{T}\right)^2}{M_{O_2}} \quad (18)$$

$$\mu_{N_2,O_2} = \frac{5}{16} \frac{\sqrt{\pi m_{N_2,O_2} k_B T}}{\pi \sigma^2_{N_2,O_2} \Omega_\mu} \quad (19)$$

where $$\Omega_\mu = \frac{1.16145}{\left(\frac{k_B T}{\varepsilon}\right)^{0.14974}} + \frac{0.52487}{\exp\left(0.77320 \frac{k_B T}{\varepsilon}\right)} + \frac{2.16178}{\exp\left(2.43787 \frac{k_B T}{\varepsilon}\right)} \quad (20)$$

and $\sigma$, $\varepsilon$ are Lennard-Jones parameters.

$$k_{N_2,O_2} = \left(C_{p,N_2,O_2} + 1.25 \frac{R}{M_{N_2,O_2}}\right) \mu_{N_2,O_2} \quad (20)$$

$$D_{water,air}[m^2/s] = -2.7756 \times 10^{-6}[m^2/s] + 4.478 \times 10^{-8}\left[\frac{m^2}{Ks}\right]T + 1.656 \times 10^{-10}\left[\frac{m^2}{K^2 s}\right]T^2 \quad (21)$$

Simulations were performed by varying various design (helix radius, pitch) operating parameters (saturator and condenser temperatures, flow rate) in turn for a 2 mm NAFION tube while maintaining them in a reasonable range as described above.

Figure 10A:
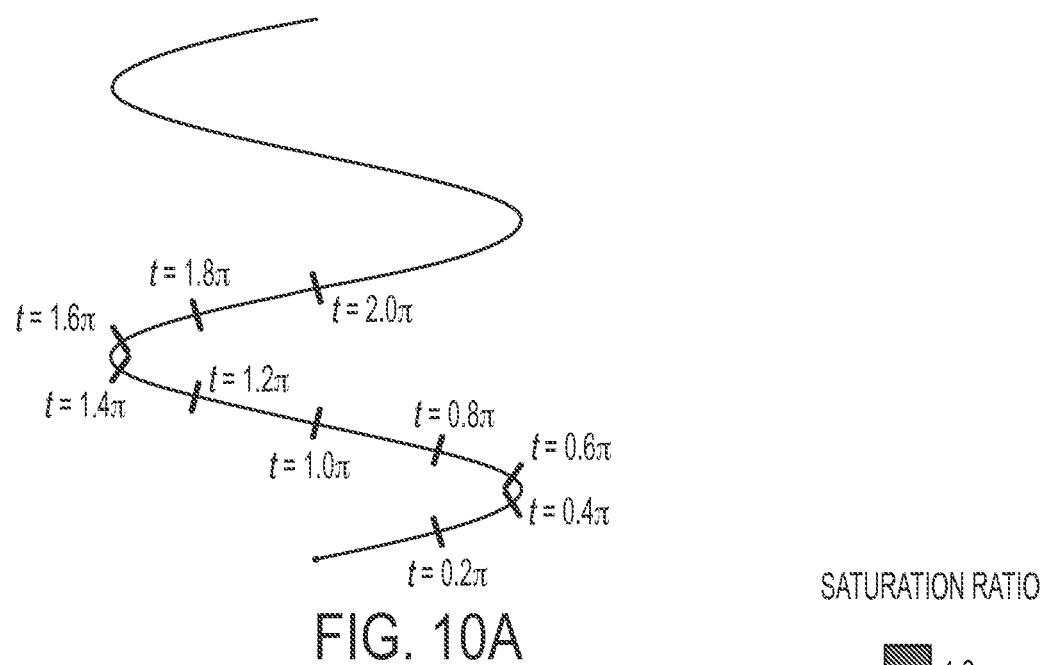
Figure 10B:
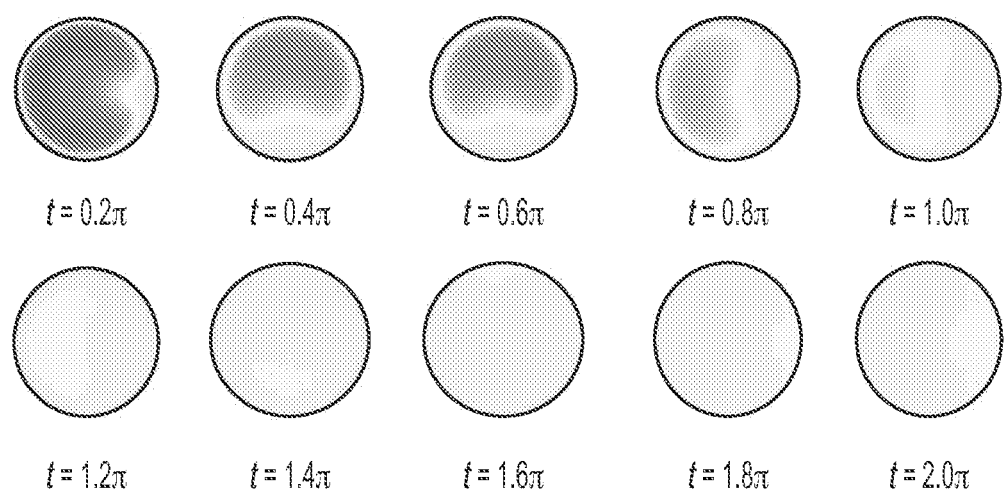
FIG. 10B shows contour plots of saturation ratios at various circular cross-sections along a helical growth tube with a first boundary condition.
Figure 12:
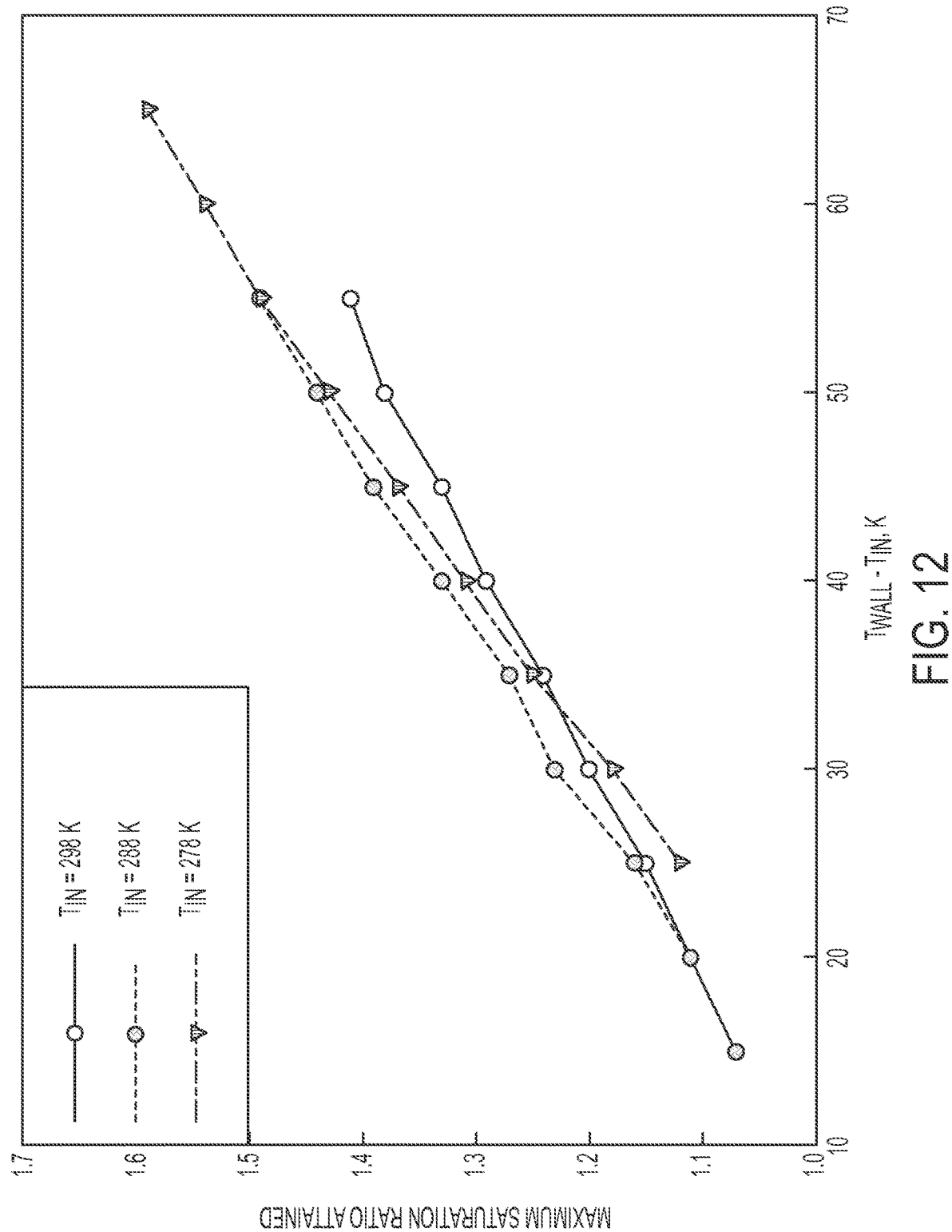
FIG. 12 is a graph showing maximum saturation ratio attained in a helical growth tube as a function of temperature differential between condenser and saturator temperatures at three different saturator temperatures.

FIGS. 10B and 11B show the saturation ratio profiles obtained in circular cross sections of the helical tube (cuts normal to the helical axis) from transport simulations, as illustrated in FIGS. 10A and 10B. The only difference between the conditions for FIGS. 10B and 11B is in the mass transfer boundary condition employed at the growth tube walls: FIG. 10B uses B.C. 1, i.e. mass transfer coefficient based flux boundary conditions, while FIG. 11B employs water saturation at the helix wall temperature described in B.C. 2. The two boundary conditions may be seen as limiting cases. The use of the flux boundary condition results in a lower water flux into the growth tube compared to the water saturation boundary condition. The saturation boundary conditions results in inward water fluxes comparable to the evaporation rate of water at the growth tube wall temperatures, while the mass transfer coefficients describe water fluxes across the membrane which are four orders of magnitude lower than the evaporation rate. Consequently, the saturation ratios achieved in FIG. 10B is lower than in FIG. 11B.

A significant feature apparent from FIGS. 10B and 11B, which was observed in all simulations performed, is that the maximum saturation ratio is achieved within the first full turn of the helix (e.g., 360° around a central helix axis). B.C. 1 results in sub-saturated regions after a full turn, which further develop into saturated regions with more turns. B.C. 2 preserves saturation in the growth tube after supersaturation is achieved and this remains conserved irrespective of the number of turns. Thus, exemplary growth tubes can be restricted to a maximum of a single helical turn to prevent evaporation of grown particles and to lower losses of grown droplets. In addition, the saturation ratios achieved in helical tubes can be lower than those achieved in straight tubes because of the enhanced mixing effects from the swirling, radial, secondary flow structures in helical tubes. The enhanced radial convective transport in the helical tube compared to a straight tube can lead to more uniform distributions of temperature and water vapor concentration, and consequent lowering of saturation ratios. Simulations also indicate that a much longer tube length (greater than 40 times the tube inner diameter) may be required to develop supersaturated regions in a cylindrical tube compared to a helical tube (typically 10 times the tube inner diameter), justifying the use of a helical tube for growth tube miniaturization. The helical coil simulations described herein also support using a helical coil design (with sufficient turns) to pre-saturate the gas stream in the saturator before passing it to the growth tube in the condenser.

As B.C. 1 resulted in comparatively lowered saturation ratios, the maximum saturation ratio achieved for this condition was chosen as a figure of merit for further analyses on the effects of design and operating parameters. The helix radius and pitch was found to have some influence on the saturation ratios achieved in the condenser tube, while the operating parameters were found to have a significantly greater impact than the helix radius and pitch. The helix diameter was varied from 10 to 40 times the tube inner diameter (based on reasonable practical winding diameters) and was found to have only a marginal effect on the maximal saturation ratio (under 1%). Lowering the pitch by a factor of 10 for a helical tube configuration of constant total length was found to lower the maximum saturation ratio achieved under 10%. Tighter helix pitches promote radial convective mixing and results in lowered saturation ratios. Higher pitches favor a slightly higher saturation ratio and lower particle loss and loss of grown particle size due to evaporation in sub-saturated zones (see FIG. 10B) when the growth tube is restricted from one half to a full turn of the helix.

FIG. 12 shows the variation in the maximum saturation ratio achieved in a tube as a function of the temperature difference between the condenser (which is the same as the growth tube walls) and saturator (identical to the temperature of the flow entering the growth tube). This operating parameter is a major driving force for heat transport and mass transport of water vapor, the differential rates of which establish supersaturation in a growth tube. This variable therefore has a strong positive effect on the figure of merit plotted on the y-axis. The calculations also demonstrate that the actual temperatures of the saturator and the condenser have a significantly smaller role compared to the temperature differential between them.

Figure 13:
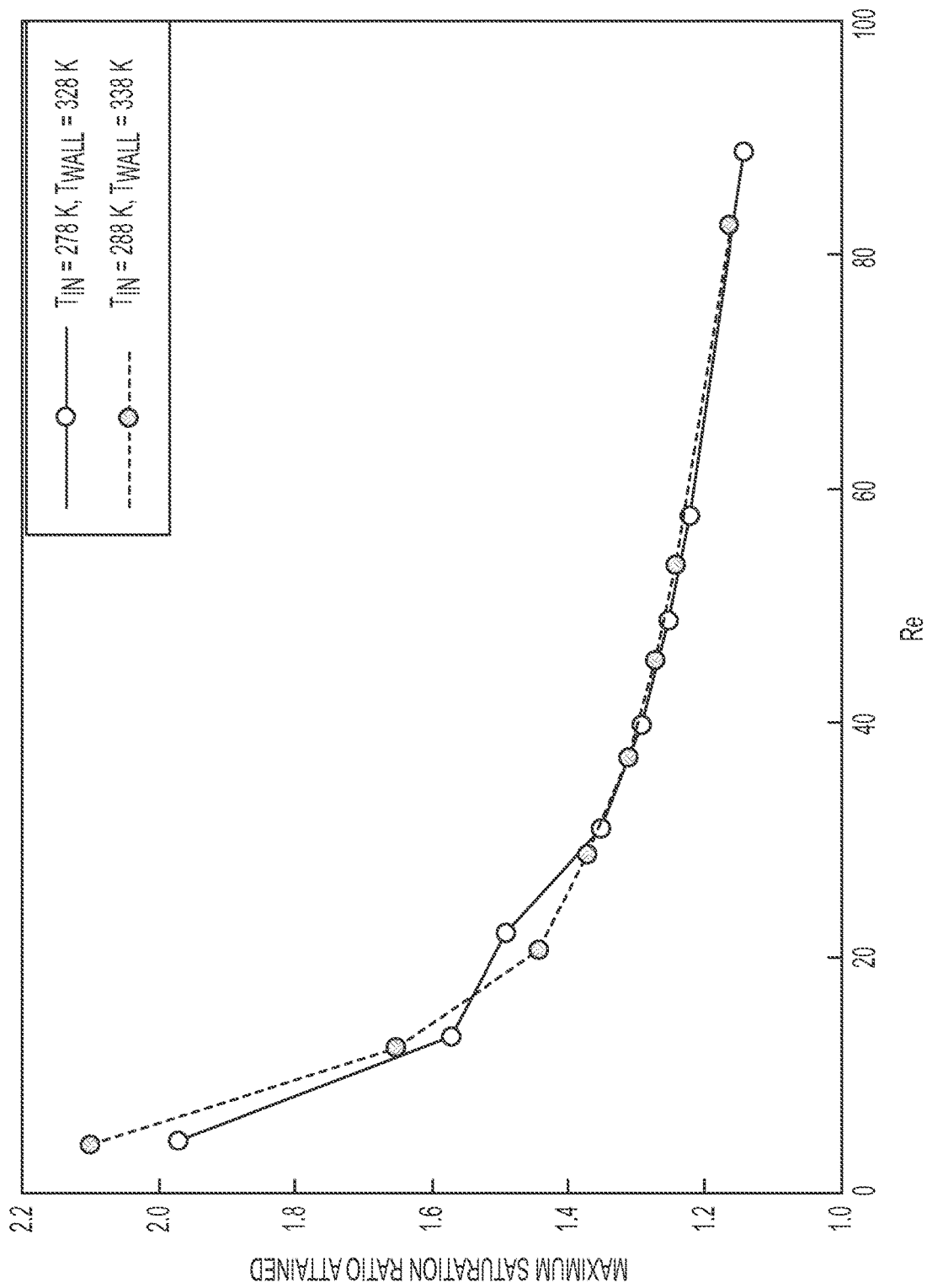
FIG. 13 is a graph showing maximum saturation ratio attained in a helical growth tube as a function of Reynolds number for a constant temperature differential.

As illustrated in FIG. 13, lower saturation ratios are achieved as the Reynolds number (based on tube diameter) is increased. Higher flow rates result in increased fluid speeds in coiled tubes and the resultant enhanced mixing arising from the heightened radial convective transport tend to level the temperature and water vapor concentrations in the inner regions of the tube. This results in lowered saturation ratios shown in FIG. 13. For the range of Reynolds numbers shown, the flow rate of air is varied from 5 to 100 mL/min in a 2 mm inner diameter NAFION tube.

Figure 14:
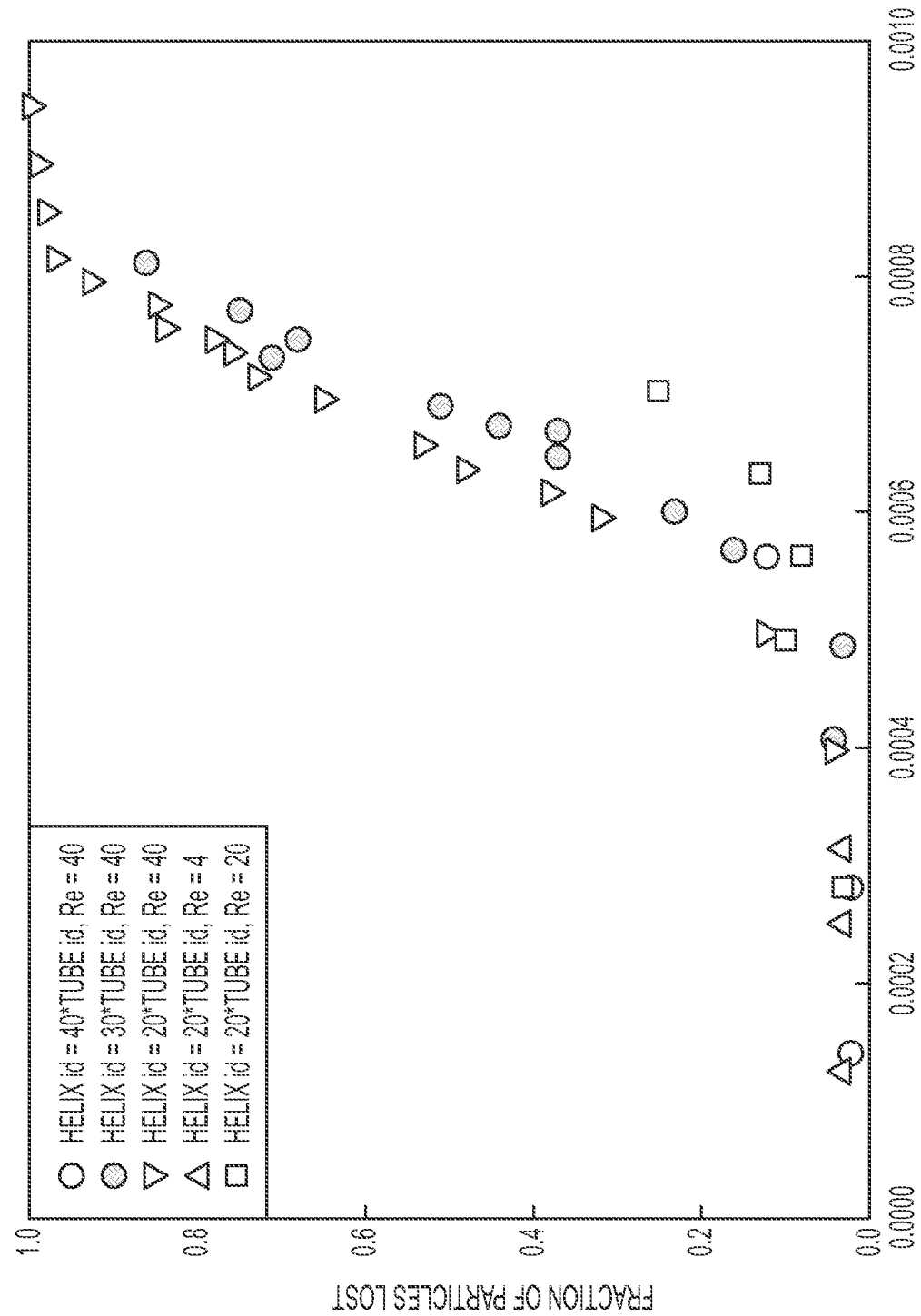
FIG. 14 is a graph showing the fraction of particles lost to walls in a helical growth tube as a function of Stokes number for different flow rates and helix radii.

An additional consideration in coiled geometries is minimization of grown droplet inertial deposition. FIG. 14 shows the results of preliminary particles loss calculations obtained from trajectory models including only fluid drag (growth is not considered and diffusive losses are not important for particles in the micrometer size range considered here). The x-axis is (Stokes number)$^{0.5}$, which is proportional to the particle radius. Stokes number, St, is a dimensionless group that evaluates the relative ratio of inertial (here centrifugal) to drag forces experienced by a particle of mass $m_p$ and friction factor f in a flow field with characteristic flow speed U. $R_{helix}$ is the helix radius, the relevant length scale for centrifugal force.

$$St = \frac{\frac{m_p U^2}{R_{helix}}}{fU} \quad (22)$$

FIG. 14 further suggests that there is a universal relationship between inertial particle loss in a helical tube and Stokes number (which is anticipated in inertial deposition). This can be exploited in the design of a helical growth tube to minimize such losses by using $St^{0.5}=0.0004$ as a starting point for design and operation.

CONCLUSIONS

The particle growth systems described herein provide numerous advantages, in particular with respect to development of low-cost, miniature systems, over known particle growth systems. Known particle growth systems use porous tubes and allow a working fluid to flow through the pores of the tube (e.g., by capillary action or gravity), and in some cases pump the working fluid to the surface of the porous tube to control its volume, pressure, etc. Thus, problems arise when these systems are re-oriented, shaken, or moved during operation. In particular, excess fluid often flows into the aerosol flow path or other parts of the system, causing further problems. The particle growth systems described herein incorporate PEMs separating a condensing fluid from an aerosol flow. Because the PEMs are substantially impermeable to bulk gases and liquids, the PEMs allow the systems to be used in any orientation and in applications involving rapid angular and/or linear vibrations or other movements, without the mass transport of fluid into the aerosol flow path. Put another way, permeation of fluid into the aerosol is mass-transfer limited, e.g., by the permeation rates provided herein.

The systems described herein are relatively low cost compared to known particle growth systems, in part because NAFION is a relatively inexpensive material and because NAFION allows the fabrication of particle growth systems having relatively simple designs. The systems described herein also require relatively low amounts of power to operate, in part because the working fluid can be transported across the PEM without consuming power, whereas many known particle growth systems require that a working fluid be carefully and actively controlled by a power-consuming pump. In some embodiments, the systems described herein require less than about 1 watt, or less than about 2 watts, or less than about 3 watts, or less than about 4 watts, or less than about 5 watts or less than about 10 watts while in use for an 8-hour shift. In some cases, the systems described herein can be provided without a heater and/or without a cooling device to further reduce the power required to operate the system.

The particle growth systems disclosed herein can facilitate the study of very small hazardous airborne particles, for example, in occupational settings. These systems facilitate the study of airborne particles having a diameter less than 300-400 nm, and as small as about 3 nm, by growing them to detectable and/or collectable sizes. In some cases, these systems can grow the airborne particles such that their diameter is at least 300 nm, or at least 400 nm, or at least 500 nm, or at least 700 nm, or at least 1 µm, or at least 2 µm, or at least 3 µm, or at least 4 µm, or at least 5 µm. These systems can sample air at a few liters per minute and concentrate particulate matter from about 1000 liters of sampled air into microliter or milliliter liquid samples for subsequent analysis. In some cases, the systems described herein can concentrate particulate matter (e.g., hazardous metal-containing particles such as mercury-containing particles) present in an aerosol at about 1 ng/m$^3$ ambient concentration to a liquid at about 10 ng/mL concentration. The airborne particles of interest can be liquid, solid, or both liquid and solid.

The systems described herein can be personal, mobile, miniature, wearable devices, such that a person can wear them in occupational settings while working. In one example, the systems described herein can be about 1"×1"×3" in size.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that illustrated embodiments are only examples and should not be considered a limitation on the scope of the disclosure. Rather, the scope of the disclosure is at least as broad as the following claims. We therefore claim as our invention all that comes within the scope of these claims.

The invention claimed is:

1. A particle growth system comprising:

an outer housing defining a liquid reservoir for containing a working liquid; and a polymer electrolyte membrane conduit positioned at least partially within the outer housing and surrounded by the reservoir, wherein the conduit includes an inlet configured to receive a particle containing gas and an outlet configured to export the particle containing gas;

wherein the system is operable to molecularly transport the working liquid into the conduit to promote particle growth in the conduit;

wherein the conduit has a helical configuration.

2. The particle growth system of claim 1, wherein the conduit is substantially impermeable to the working liquid.

3. The particle growth system of claim 1, further comprising a heating element configured to heat the liquid in the reservoir.

4. The particle growth system of claim 1, further comprising a cooling device configured to cool a portion of the conduit.

5. The particle growth system of claim 1, wherein the working liquid is either liquid water or a liquid alcohol.

6. The particle growth system of claim 1, further comprising a particle detection system coupled to the outlet of the conduit.

7. The particle growth system of claim 1, further comprising a particle counting system coupled to the outlet of the conduit.

8. The particle growth system of claim 1, further comprising a particle collection system coupled to the outlet of the conduit.

9. The particle growth system of claim 1, further comprising a source of the particle-containing gas coupled to the inlet of the conduit.

10. The particle growth system of claim 1, wherein the conduit comprises:

a porous support conduit not made from a polymer electrolyte membrane; and a polymer electrolyte membrane substantially covering the pores of the porous support conduit to render the porous support conduit substantially impermeable to the working liquid in the reservoir.

11. The particle growth system of claim 1, further comprising a second polymer electrolyte membrane conduit positioned at least partially within the outer housing and surrounded by the reservoir.

12. The particle growth system of claim 1, wherein the system is operable to molecularly transport the working liquid into the conduit by a mechanism consisting essentially of molecular transport of individual molecules of the working liquid across the membrane.

13. The particle growth system of claim 1, wherein the conduit extends no more than 360° around a central helix axis.

14. The particle growth system of claim 1, wherein the conduit has a length along a helical path that is at least 40 times an inner diameter of the conduit.

15. The particle growth system of claim 1, wherein the conduit defines a helix diameter that is at least 10 times an inner diameter of the conduit.

16. The particle growth system of claim 1, wherein the conduit is configured such that a particle in a particle containing gas flowing through the conduit has a Stokes number such that the square root of the Stokes number is no greater than 0.0004.

17. The particle growth system of claim 1, wherein the conduit has a helical configuration with $St^{0.5}<0.0004$, where St is Stokes number.

18. A method of growing particles in a particle growth system comprising:

providing the particle growth system of claim 1;

introducing a working fluid into the liquid reservoir;

introducing a particle containing gas into the conduit;

allowing the working fluid to be molecularly transported across the polymer electrolyte membrane into the conduit; and allowing the working fluid to condense onto particles in the gas in the conduit.

19. The method of claim 18, further comprising maintaining a first portion of the conduit at a first temperature and maintaining a second portion of the conduit at a second temperature, wherein the first temperature is different from the second temperature.

20. The method of claim 18 further comprising collecting grown particles at the outlet of the conduit.

21. The method of claim 18, further comprising detecting grown particles at the outlet of the conduit.

22. The method of claim 18, further comprising counting grown particles at the outlet of the conduit.

23. The method of claim 18, further comprising analyzing grown particles at the outlet of the conduit.

24. The method of claim 18, wherein particles in the particle containing gas flowing through the conduit have a Stokes number such that the square root of the Stokes number is no greater than 0.0004.

25. The method of claim 18, wherein the particle containing gas flows through the conduit with a Reynolds number of at least 20.

26. The method of claim 18, wherein a saturation ratio of the working fluid in the conduit reaches 1.0 or lower within one full turn of the helical conduit.

27. The method of claim 18, wherein a difference between a temperature of a condensor portion of the particle growth system and a temperature of a saturator portion of the particle growth system is no greater than 50° K.

28. The method of claim 18, wherein the conduit is generally helical with $St^{0.5}<0.0004$, where St is Stokes number.

29. A particle growth system comprising:

a first channel, having a first inlet and a first outlet, for containing a working liquid;

a second channel having a second inlet configured to receive a particle containing gas and a second outlet configured to export the particle containing gas, the first and second channels being microfluidic channels; and a polymer electrolyte membrane portion separating the first channel from the second channel;

wherein the system is operable to molecularly transport the working liquid into the second channel to promote particle growth in the second channel.

30. The system of claim 29, wherein the polymer electrolyte membrane (PEM) portion comprises a third channel having a first PEM wall in communication with the first channel and a second PEM wall in communication with the second channel, and a space between the first and second PEM walls, such that the system is operable to molecularly transport the working liquid from the first channel, through the first PEM wall, across the space, through the second PEM wall, and into the second channel.

* * * * *